Figure 2A:
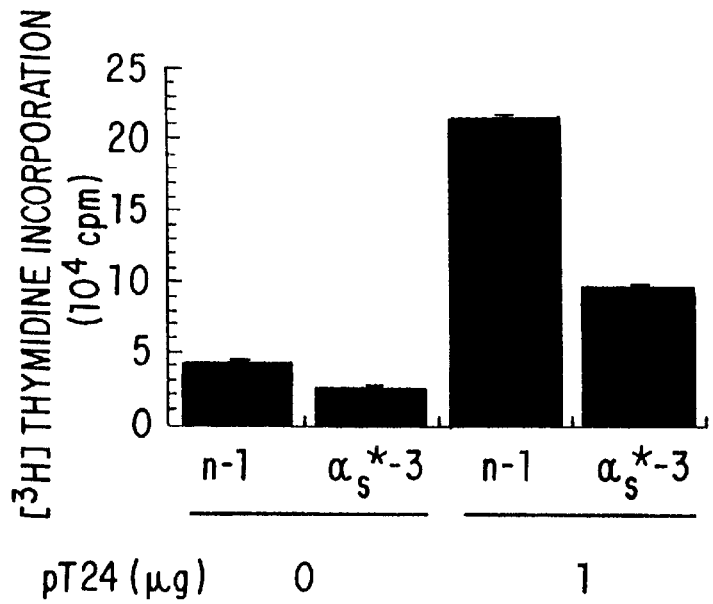

United States Patent [19]
Iyengar

[11] Patent Number: 6,034,071
[45] Date of Patent: *Mar. 7, 2000

[54] MUTANT ACTIVATED $G_S\alpha$ AND ADENYLYL CYCLASE 2 FOR USE AS THERAPEUTIC AGENTS

[76] Inventor: Srinivas Ravi V. Iyengar, 3254 S. Shelly St., Mohegan Lake, N.Y. 10547

[*] Notice: This patent issued on a continued prosecution application filed under 37 CFR 1.53(d), and is subject to the twenty year patent term provisions of 35 U.S.C. 154(a)(2).

[21] Appl. No.: 08/307,896

[22] Filed: Sep. 16, 1994

[51] Int. Cl.[7] ...................................................... A61K 47/36
[52] U.S. Cl. ............................................. 514/44; 536/23.5
[58] Field of Search ............................... 514/44; 536/23.5

[56] References Cited

PUBLICATIONS

Report and Recommendations of the Panel to Assess the NIH Investment in Research on Gene Therapy, Orkin et al (Co–Chairs), Dec. 7, 1995.
Premont et al., Meth. Enzymol. 238:116–127, 1994.
Cowley et al., Cell 77:841–852, 1994.
Chen et al., Science 263:1278–1281, 1994.
Iyengar, R., FASEB J. 7:768–775, 1993.
Pieroni et al., Curr. Opin. Neurobiol. 3:345–351, 1993.
Jacobowitz et al., J. Biol. Chem. 268:3829–3832, 1993.
Yoshimura et la., J. Biol. Chem. 268:4604–4607, 1993.
Marx Science 260:1588–1590, 1993.
Taussig et al., J. Biol. Chem. 268:9–12, 1993.
Graves et al., Proc. Natl. Acad. Sci. USA 90:10300–10304, 1993.
Assender et al., Biochem. J. 288:527–532, 1992.
Stengel et al., Hum. Genet. 90:126–130, 1992.
Federman et al., Nature 356:159–161, 1992.
DeVivo et al., J. Biol. Chem. 267:18263–18266, 1992.
Levine, M., N. Engl. J. Med. 325:1738–1740, 1991.
Weinstein et al., N. Engl. J. Med. 325:1688–1695, 1991.
Feinstein et al., Proc. Natl. Acad. Sci. USA 88:10173–10177, 1991.
Bourne et al., Nature 349:117, 1991.
Landis et al., Nature 340:692–696, 1989.
van Corven et al., Cell 59:45–54, 1989.
Gilman, A., Ann. Rev. Biochem. 56:615–649, 1987.
Clegg et al., J. Biol. Chem. 262:13111–13119, 1987.
Dickson et al., Science 232:1540–1543, 1986.
Mattera et al., FEBS 206:36–42, 1986.
Harris et al., Science 229:1274–1277, 1985.

*Primary Examiner*—James Martinell
*Attorney, Agent, or Firm*—Baker & Botts; Richard S. Clark

[57] ABSTRACT

The present invention relates to therapeutic uses of mutant activated $G_s\alpha$ and adenylyl cyclase 2. Although mutant activated $G_s\alpha$ has been, previously, associated with proliferative and physiological disorders of a subset of differentiated cells, it has now been discovered that mutant activated $G_s$ $\alpha$ (referred to, hereafter, as $G_s\alpha^*$) can suppress proliferation as well as the transformed phenotype. Accordingly, in various embodiments of the present invention, introduction of $G_s\alpha^*$ into cells or tissues, preferably by the use of viral vectors, may be used to reduce proliferation and/or prevent the development, reduce, or reverse malignancy. In further embodiments of the present invention, the introduction of adenylyl cyclase 2, preferably using viral vectors, may be used to limit cell proliferation and/or reduce the transformed phenotype. Because adenylyl cyclase 2 is not endogenous to most tissues but can be activated in a subset of malignant or otherwise proliferative cells (e.g., those in which growth factors stimulate phospholipases C and/or D), the introduction of adenylyl cyclase 2 may be used to selectively increase cAMP levels and thereby prevent, reduce, or reverse proliferation and/or malignancy and thus relieve the pathophysiological state.

9 Claims, 28 Drawing Sheets

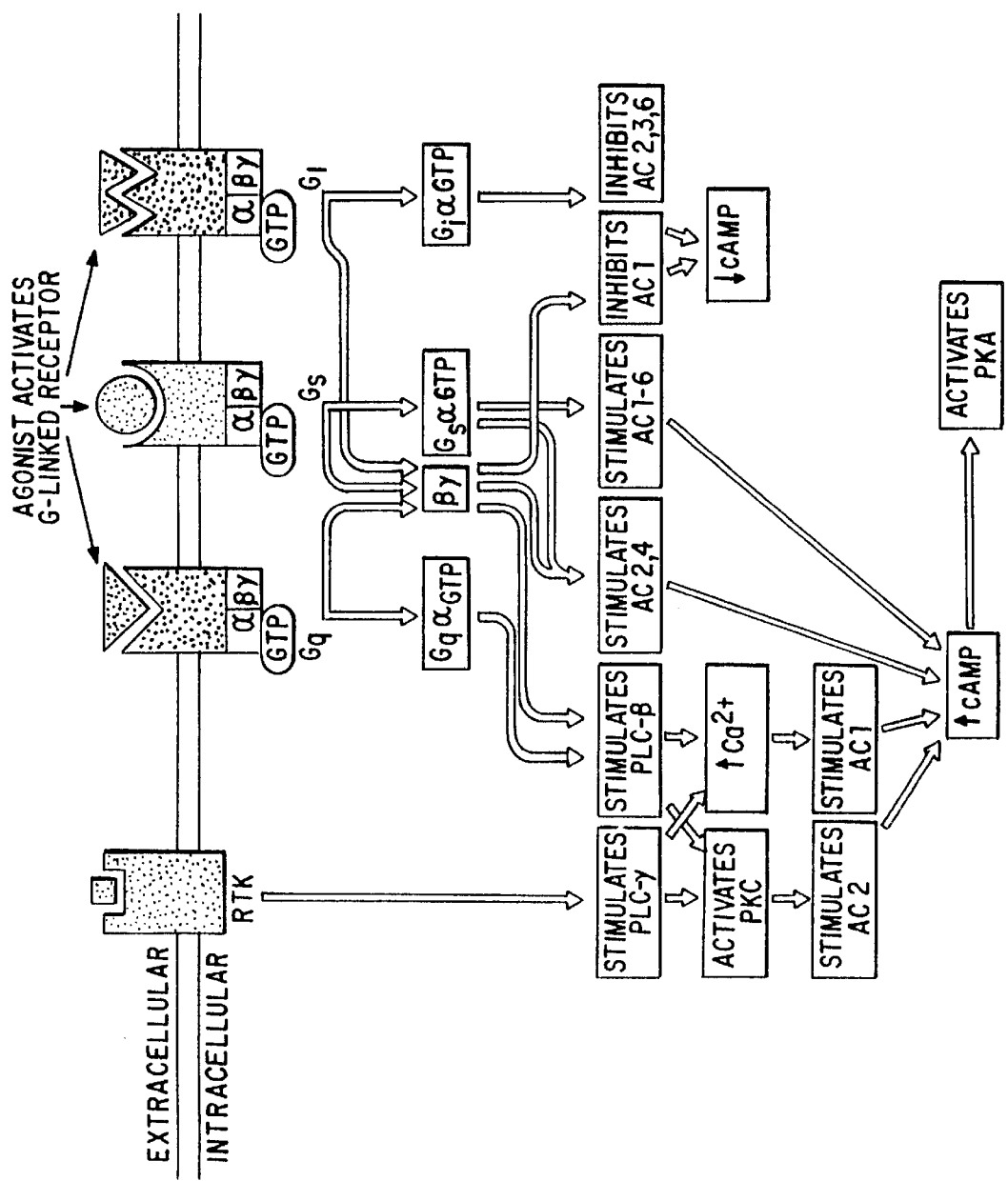

Figure 7D:
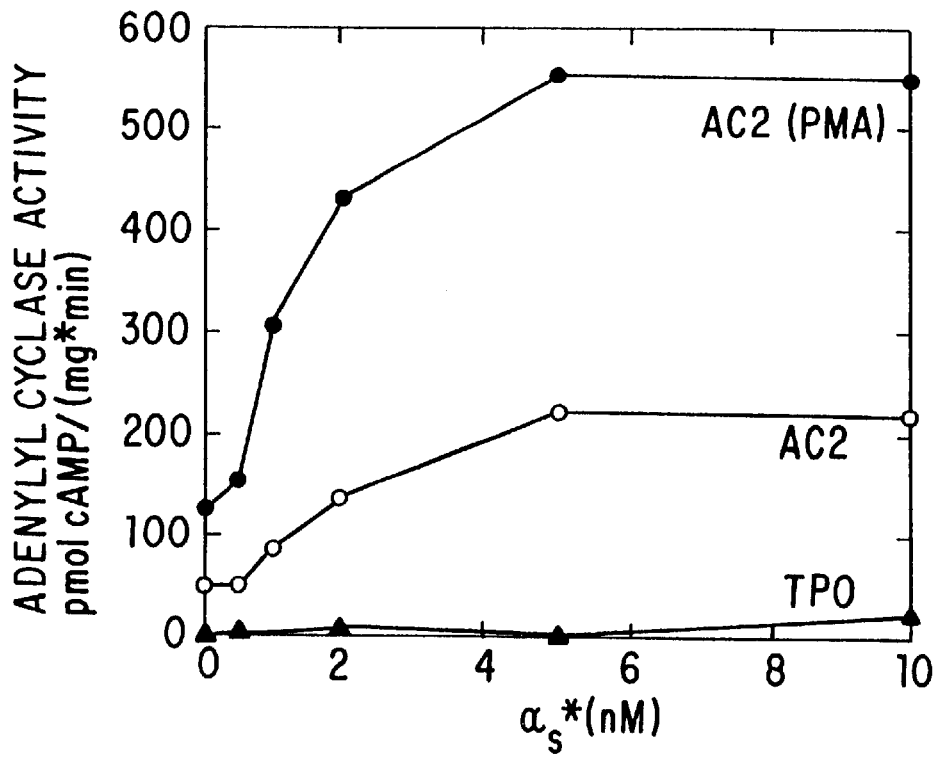

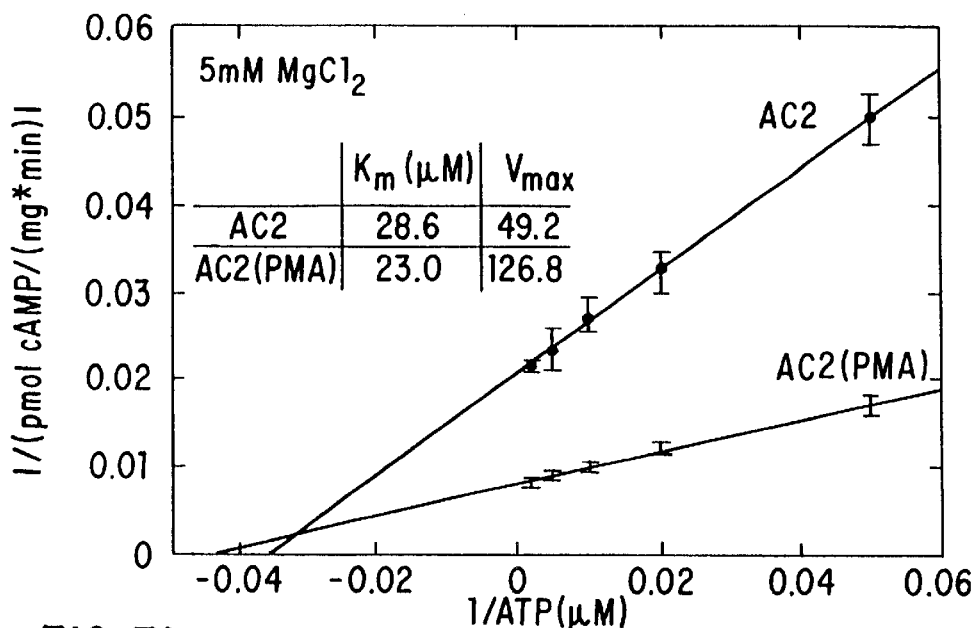
FIG. 7A
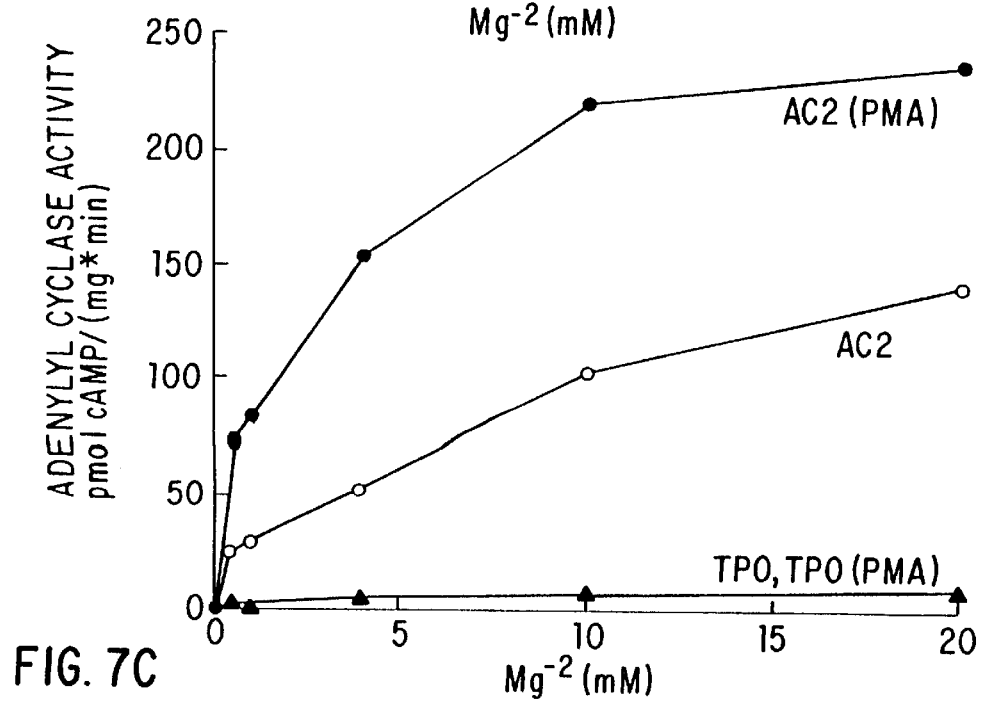
FIG. 7B
FIG. 7C

MGCLGNSKTEDQRNEEKAQREANKKIE

KQLQKDKQVYRATHRLLLLGAGESGKST

IVKQMRILHVNGFNGDSEKATKVQDIK

NNLKEAIETIVAAMSNLVPPVELANPEN

QFRVDYILSVMNVPDFDFPPEFYEHAKA

LWEDEGVRACYERSNEYQLIDCAQYFL

DKIDVIKQADYVPSDQDLLRCRVLTSGIF

ETKFQVDKVNFHMFDVGGQRDERRKW

IQCFNDVTAIIFVVASSSYNMVIREDNQ

TNRLQEALNLFKSIWNNRWLRTISVILF

LNKQDLLAEKVLAGKSKIEDYFPEFARY

TTPEDATPEPGEDPRVTRAKYFIRDEFL

RISTASGDGRHYCYPHFTCAVDTENIRR

VFNDCRDIIQRMHLRQYELL

FIG. 11A

Nucleotide Sequence for human G$_s$-α gccgccgccgccatgggctgcctcgggaacagtaagaccgaggaccagcgcaacgaggagaa
ggcgcagcgtgaggccaacaaaaagatcgagaagcagctgcagaaggacaagcaggtctacc
gggccacgcaccgcctgctgctgctgggtgctggagaatctggtaaaagcaccattgtgaagc
agatgaggatcctgcatgttaatgggtttaatggagacagtgagaaggcaaccaaagtgcagg
acatcaaaaacaacctgaaagaggcgattgaaaccattgtggccgccatgagcaacctggtgc
cccccgtggagctggccaaccccgagaaccagttcagagtggactacatcctgagtgtgatga
acgtgcctgactttgacttccctcccgaattctatgagcatgccaaggctctgtggggaggatga
aggagtgcgtgcctgctacgaacgctccaacgagtaccagctgattgactgtgcccagtactt
cctggacaagatcgacgtgatcaagcaggctgactatgtgccgagcgatcaggacctgcttcg
ctgccgtgtcctgacttctggaatctttgagaccaagttccaggtggacaaagtcaacttccac
atgtttgacgtgggtggccagcgcgatgaacgccgcaagtggatccagtgcttcaacgatgtg
actgccatcatcttcgtggtggccagcagcagctacaacatggtcatccgggaggacaaccag
accaaccgcctgcaggaggctctgaacctcttcaagagcatctggaacaacagatggctgcgc
accatctctgtgatcctgttcctcaacaagcaagatctgctcgctgagaaagtccttgctggga
aatcgaagattgaggactactttccagaatttgctcgctacactactcctgaggatgctactcc
cgagcccggagaggacccacgcgtgacccgggccaagtacttcattcgagatgagtttctgag
gatcagcactgccagtggagatgggcgtcactactgctaccctcatttcacctgcgctgtgga
cactgagaacatccgccgtgtgttcaacgactgccgtgacatcattcagcgcatgcacttcg
tcagtacgagctgctctaagaagggaacccccaaatttaattaaagccttaagcacaattaatt
aaaagtgaaacgtaattgtacaagcagttaatcacccaccatagggcatgattaacaaagcaa
cctttcccttcccccgagtgattttgcgaaaccccctttcccttcagcttgcttagatgttcca
aatttagaaagcttaaggcggcctacagaaaaaggaaaaaaggccacaaaagttccctctcac
tttcagtaaaaataaataaaacagcagcagcaaacaaataaaatgaaataaaagaaacaaatg
aaataaatattgtgttgtgcagcattaaaaaaaatcaaaataaaaattaaatgtgagcaaag

FIG. 11B

MRRRYLRDRAEAAAAAGGGEGLQRSRDWLYESYYCMSQQHPLIVFLLLIVMGACLALLAV
FFALGLEVEDHVAFLITVPTALAIFFAIFILVCIESVFKKLLRVFSLVIWICLVAMGYLFMCFGGT
VSAWDQVSFFLFIFVVYTMLPFNMRDAIIASILTSSSHTIVLSVYLSATPGAKEHLFWQILANV
IIFICGNLAGAYHKHLMELALQQTYRDTCNCIKSRIKLEFEKRQQERLLLSLLPAHIAMEMKAEIIQ
RLQGPKAGQMENTNNFHNLYVKRHTNVSILYADIVGFTRLASDCSPGELVHMLNELFGKFDQIA
KENECMRIKILGDCYYCVSGLPISLPNHAKNCVKMGLDMCEAIKKVRDATGVDINMRVGVHSGN
VLCGVIGLQKWQYDVWSHDVTLANHMEAGGVPGRVHISSVTLEHLNGAYKVEEGDGEIRDPYL
KQHLVKTYFVINPKGERRSPQHLFRPRHTLDGAKMRASVRMTRYLESWGAAKPFAHLHHRDSM
TTENGKISTTDVPMGQHNFQNRTLRTKSQKKRFEELNERMIQAIDGIINAQKQWLKSEDIQRISL
LFYNKNIEKEYRATALPAFKYYVTCACLIFLCIFIVQILVLPKTSILGFSFGAAFLSLIFILFVCFA
GQLLQCSKKASTSLMWLLKSSGIIANRPWPRISLTIVTAIILTMAVFNMFFLSNSEETTLPTAN
TSNANVSVPDNQASILHARNLFFLPYFIYSCILGLISCSVFLRVNYELKMLIMMVALVGYNTILLH
THAHVLDAYSQVLFQRPGIWKDLKTMGSVSLSIFFTLLVLGRQSEYYCRLDFLWKNKFKKEREE
IETMENLNRVLLENVLPAHVAEHFLARSLKNEELYHQSYDCVCVMFASIPDFKEFYTESDVNKEG
LECLRLLNEIIADFDDLLSKPKFSGVEKIKTIGSTYMAATGLSAIPSQEHAQEPERQYMHIGTMVE
FAYALVGKLDAINKHSFNDFKLRVGINHGPVIAGVIGAQKPQYDIWGNTVNVASRMDSTGVLD
KIQVTEETSLILQTLGYTCTCRGIINVKGKGDLKTYFVNTEMSRSLSQSNLAS

FIG. 12A

MWLLKSSGIIANQPWPRISLTIITTAIILMMAVFNMFFLSDSEETIPPTANTTNTS
FSASNNQVAILRAQNLFFLPYFIYSCILGLISCSVFLRVNYELKMLIMMVALVGYN
TILLHTHAHVLGDYSQVLFERPGIWKDLKTMGSVSLSIFFITLLVLGRQNEYYCRL
DFLWKNKFKKEREEIETMENLNRVLLENVLPAHVAEHFLARSLKNEELYHQSYDC
VCVMFASIPDFKEFYTESDVNKEGLECLRLLNEIIADFDDLLSKPKFSGVEKIKTIG
STYMAATGLSAVPSQEHSQEPERQYMHIGTMVEFAFALVGKLDAINKHSFNDFKL
RVGINHGPVIAGVIGAQKPQYDIWGNTVNVASRMDSTGVLDKIQVTEETSLVLQ
TLGYTCTCRGIINVKGKGDLKTYFVNTEMSRSLSQSNVAS

FIG. 12B

```
cccgggcagcgcgctctgcggtcgcctaccgctgcgcccccgccgccgcgcgacgtggcagaggcgatgc
ggcgccgctacctgcgggaccgcggccgcgagccggcggcgcagcgcggcgcagcaccgctcatgtcttcctgctg
agcggtcccggactgctctacagtcctacctgtagccgtcttctcgccgtcttcttgaaggtgaagaccatgt
ctcatcgtcatgggcgcctgcctctgccctgtagccgctggcctgccatttcttgctgcatagagtctgt
gcattttaataacggttcccactgtgtgtttcgctgtgattggatatgtcgttgccatggatacctgttcatgtctt
tcaagaagctactccgtgtgtctgcctggaccaggtgtcattcttcctcttcatcatctttgtgtatataccatgcttcc
cggagggactgtgtctgcctggaccaggtgtcattcttcctcttcatcatctttgtgtatataccatgcttcc
cttcaacatgcgagatgccatcattgccagcatcctcacatcttcatctatacgatagtgctgagcgtctacct
gtctgcaacaccagggcctaccaagagcacctcatggagctgcctgcagcaaacctatcgggacacgtaattgc
acttgcggagcctaccacaagcacctcatggagctgcctgcagcaaacctatcgggacacgtaattgc
atcaagtccgatcaagctgaatttgaaaaacgcagcaggaacgctctctcctgctgccagctca
catgccatggagagaagctgaaatcattcagaggctgcagggcccaaagcaggacagatgaaaacaca
aacaacttccacaatctgtatgtcaaacgacacaccaacgtgagcatgctgaatgaactcttggaagtttgatcaaa
ccgccttgcaagcgattgctccctggcgaactgtccacatgctgaatgaactcttggaagtttgatcaaa
tagcaaagagagaatgcatgagaactgctattactgttccggctctccctatat
cactcctaaccatgccaagaactgtgtgaaatgggattggatatgtgcgaagccataaaagtgaggat
gctaccggagtgtatatcaacatgcgtgtaggagtgcattctgggaacgttcctgtgtgtgattggtctccag
aagtggcagtatgatgtgtgtctcatgatgttactctgcaaaccacacatggaagctggaggagtccctgggcg
tgttcacatttcttcagtcagtccctgagcactgtgaaaccctacttgtaatcatcccaagggagagcgacggagtcctc
agacccatatttaaagcagacctggtgaaaacctacttgtaatcatcccaagggagagcgacggagtcctc
agcatctcttcagacctcgacactcgacaccatcgacaggagccaagatgagagcatcgtccgcatgaccgtacttg
gagtctggggagcagccaagccattcgcaatgggtcaatgtcaacatatttcaaatcgcacttaagaactaagctcacagaagaag
ttagtaccacggatgtgccaatgggtcaatgtcaacatatttcaaatcgcacttaagaactaagctcacagaagaag
agatttgaagagaaactgaatgaaaggatgatcaaaggatccctgtttctataacaagaatatagaaagaaaataccgactactgcac
gtcagagacattcaaagaatccctgtttctataacaagaatatagaaagaaaataccgactactgcac
tgccagcagcaagtactacgtgcctgcctcatcgtgtacagatacttgtatt
gccaaaacgtccatctccttggcttctccttgagctgcattctctcctcatcttcatctcctttgtctgcttc
```

FIG. 12C

```
gctggacagctttgcaatgcagcagcaaaaaggcctccacctctcatgtggctttgaaatcatcaggcatcat
cgccaaccgcccatgccacgcggatctccctcacaatgcctgccatctcatcaccatggctgtgttca
acatgtttttcctgagcaactctgaaatctccactgccaatacatcaaatgcaaacgtttctgtc
ccgataaccaggcgtcgattcttcatgctcgaaactgttttcctccctacttcatatacagctgcatcctgg
gcttgatctcctgctccgtttctgaggtgaactatgagttaaaaatgttaatcatgatggtggcactgtgg
gctacaacaccattctactccacacaccatgcccatgttctgatgcgtacagcaggtcctgtttcagagacca
ggcatttggaaagaccgaagaccatgggctccgtcactctccatattcttcatcacgctcggttctgggc
agacagagtgaatattactgtaggttagacttctgtggaagaacaagttcaaaaagagcgggaggagataga
aaccatgagaacctaaatcgagtgctgctgaccaccagtgcttcctgcacacgtggctgaacacttcctgcca
ggagcctgaaaaatgaggagagctgtaccaccagtcctacgactgtcgtctgtcatgtttgcctccattccgac
ttcaaggagttcacacagagtcacagatgtgaacaagaaggcttgaatgcctgcggctcggaatgagatcat
tgctgacttgatgatctgctttctaagccaaagttcagtgtgttgaaagatcaagaccaatgggagcacata
catgcagccacggactgagtgccataccccaggagcacgcccaggaacctgagcgtcagtacatgcac
ataggcaccatgtgtgagtttgcatatgccctgtgtgggaaaactgatgccatcaataagcactccttcaacga
cttcaaactgcgagtgggtatcaaccatgggctcctaatagctggcgtcatagggggctcaaaagccacagtatg
acatctgggcaacactgtcaacgtgcagacgcttgcagacgcttggctacacgtgcgaggtatcatcaatgtgaaggga
tgaggagacaagcctcatcttgcagacatatttgtaaacacagagatgtcaaggtccctttctcagagcaacttggcatcctga
aaggggacctgaagacatatttgtaaacacagagaatgtacttgcaggaaggtaccacgcactttctgactgcaaccctcc
gaagctgtctctcctgacaagaagaatgtacttgcaggaaggtaccacgcactttctgactgcaaccctcc
cttcgtcctgatgtacgtgctctgccccatcctctgagcccactgtcctgctgtctcctaagcagaggaagga
ctgtttggtgtctgcgtgccggagagcattgaagaagtgatgaagaggtgaagtgaacacacattcttaaggcaataaa
accatgtcctgaagtggtgtatattatctctggtgtcattgtgaatagctgaataagctgtaactgcatcctagt
acgggggtgtatattatctctggtgtcattgtgaataagctgatccgtcacccaacatagctcgtaactgcatcctagt
ctgatatcaaacacacagtgccatgccatcacacagtctgagactctcagctctgtcctcctgttgttcacctacca
tgtgtctcattgccagtgtgctcttgggggtcctgggggtctcagctgagctcgtctgagactcacgaccagtttgtaccaaactca
tgtgcagcagcgttgccatccatcaccacagttgccatccaccagaattagtctcacagcctagcctagactccacagtttgtaccaaactca
tctgatgtttttgatgcattgtcaaaagttcattcattaaaagtttatgtacttgaaaaaaa
```
FIG. 12C cont.

```
attgtgcagattctcgtgctgccaaaaacgtctgtcctgggcatctcctttggggctgcgtttc
tcttgctggccttcatcctcttcgtctgctttgctggacagcttctgcaatgcagcaaaaaagc
ctctcccctgctcatgtggcttttgaagtcctcgggcatcattgccaaccagccctggccacgg
atctctctcacgatcatcaccacagccatcatattaatgatggccgtgttcaacatgtttttcc
tgagtgactcagaggaaacaatccctccaactgccaacacaacaaacacaagcttttcagcct
caaataatcaggtggcgattctgcgtgcgcagaatttattttttcctcccgtactttatctacag
ctgcattctgggactgatatcctgttccgtgttcctgcgggtaaactatgagctgaagatgttg
atcatgatggtggccttggtgggctacaacaccatcctactccacacccacgcccacgtcctg
ggcgactacagccaggtcttatttgagagaccaggcatttggaaagacctgaagaccatgggc
tctgtgtctctctctatattcttcatcacactgcttgttctgggtagacagaatgaatattactg
taggttagacttcttatggaagaacaaattcaaaaaagagcgggaggagatagagaccatgga
gaacctgaaccgcgtgctgctggagaacgtgcttcccgcgcacgtggctgagcacttcctggc
caggagcctgaagaatgaggagctataccaccagtcctatgactgcgtctgcgtcatgtttgc
ctccattccggatttcaaagaattttatacagaatccgacgtgaacaaggagggcttggaatgc
cttcggctcctgaacgagatcatcgctgactttgatgatcttctttccaagccaaaattcagtg
gagttgaaaagattaagaccattggcagcacatacatggcagcaacaggtctgagcgctgtgc
ccagccaggagcactcccaggagcccgagcggcagtacatgcacattggcaccatggtggag
tttgcttttgccctggtagggaagctggatgccatcaacaagcactccttcaacgacttcaaat
tgcgagtgggtattaaccatggacctgtgatagctggtgtgattggagctcagaagccacaata
tgatatctggggcaacactgtcaatgtggccagtaggatggacagcaccggagtcctggacaa
aatacaggttaccgaggagacgagcctcgtcctgcagaccctcggatacacgtgcacctgtcg
aggaataatcaacgtgaaaggaaagggggacctgaagacgtactttgtaaacacagaaatgtc
aaggtccctttcccagagcaacggcatcctgaagagtcaccttcatttggcaagaagactg
tattttcaggaaggtatcacacactttctgactgcaacttctgtcccttgttttgatgtgcgtg
ctgtctgtcctatggagcctctgcagactcgttctcgtgacccagtggcataccgtttggtgtc
tgatgtgtgcccagatcgttctgccacttgcactgtgcttgctcctaagcaaaagggaaaagga
gcgcgcgtgatagaagaaaagcactgggagaactaacagaggagaaaggtgaaacacacaca
cattcttaaggcaataaaactaggggtgtatattatcttctggtgcatgttctttctggaaaa
tatggtagctcgccaaccgcatctgctcatctgatattcaaacacacagtattcgtgaataagt
tgattctgtccccacgtggactctgtgctcacccattgtctcattgccagtggtgtccaaggg
cccccgttgggacccacggctctcgtccctctgctccgtgtgtctcatgccagcagcacgtcg
ccatccgtcaccagaattagtcctcacagcctaggaccagttttgtatcaaactcgtctgatgt
tttgatgccatttgtcttttgtaaagttaattcattaaaagttttatgtactttga
```

FIG. 12D

SEQUENCE LISTING

<160> NUMBER OF SEQ ID NOS: 9

<210> SEQ ID NO 1
<211> LENGTH: 380
<212> TYPE: PRT
<213> ORGANISM: Homo sapiens

<400> SEQUENCE: 1

```
Met Gly Cys Leu Gly Asn Ser Lys Thr Glu Asp Gln Arg Asn Glu Glu
 1               5                  10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
            100                 105                 110

Arg Val Asp Tyr Ile Leu Ser Val Met Asn Val Pro Asp Phe Asp Phe
        115                 120                 125

Pro Pro Glu Phe Tyr Glu His Ala Lys Ala Leu Trp Glu Asp Glu Gly
    130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
                165                 170                 175
```

```
Val Pro Ser Asp Gln Asp Leu Leu Arg Cys Arg Val Leu Thr Ser Gly
            180                 185                 190

Ile Phe Glu Thr Lys Phe Gln Val Asp Lys Val Asn Phe His Met Phe
        195                 200                 205

Asp Val Gly Gly Gln Arg Asp Glu Arg Arg Lys Trp Ile Gln Cys Phe
        210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
                245                 250                 255

Asn Leu Phe Lys Ser Ile Trp Asn Asn Arg Trp Leu Arg Thr Ile Ser
            260                 265                 270

Val Ile Leu Phe Leu Asn Lys Gln Asp Leu Leu Ala Glu Lys Val Leu
        275                 280                 285

Ala Gly Lys Ser Lys Ile Glu Asp Tyr Phe Pro Glu Phe Ala Arg Tyr
        290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
                325                 330                 335

Ala Ser Gly Asp Gly Arg His Tyr Cys Tyr Pro His Phe Thr Cys Ala
            340                 345                 350

Val Asp Thr Glu Asn Ile Arg Arg Val Phe Asn Asp Cys Arg Asp Ile
        355                 360                 365

Ile Gln Arg Met His Leu Arg Gln Tyr Glu Leu Leu
        370                 375                 380

<210> SEQ ID NO 2
<211> LENGTH: 1516
<212> TYPE: DNA
<213> ORGANISM: Homo sapiens

<400> SEQUENCE: 2
gccgccgccg ccatgggctg cctcgggaac agtaagaccg aggaccagcg caacgaggag      60
aaggcgcagc gtgaggccaa caaaaagatc gagaagcagc tgcagaagga caagcaggtc     120
taccgggcca cgcaccgcct gctgctgctg ggtgctggag aatctggtaa aagcaccatt     180
gtgaagcaga tgaggatcct gcatgttaat gggtttaatg agacagtga aaggcaacc      240 aaagtgcagg acatcaaaaa caacctgaaa gaggcgattg aaaccattgt ggccgccatg     300
agcaacctgg tgcccccgt ggagctggcc aaccccgaga accagttcag agtggactac      360
atcctgagtg tgatgaacgt gcctgacttt gacttccctc ccgaattcta tgagcatgcc     420
aaggctctgt gggaggatga aggagtgcgt gcctgctacg aacgctccaa cgagtaccag     480
ctgattgact gtgcccagta cttcctggac aagatcgacg tgatcaagca ggctgactat     540
gtgccgagcg atcaggacct gcttcgctgc cgtgtcctga cttctggaat ctttgagacc     600
aagttccagg tggacaaagt caacttccac atgtttgacg tgggtggcca gcgcgatgaa     660
cgccgcaagt ggatccagtg cttcaacgat gtgactgcca tcatcttcgt ggtggccagc     720
agcagctaca catggtcat ccgggaggac aaccagacca accgcctgca ggaggctctg      780
aacctcttca gagcatctg gaacaacaga tggctgcgca ccatctctgt gatcctgttc      840
ctcaacaagc aagatctgct cgctgagaaa gtccttgctg ggaaatcgaa gattgaggac     900
tactttccag aatttgctcg ctacactact cctgaggatg ctactcccga gcccggagag     960
```

-continued

```
gacccacgcg tgacccgggc caagtacttc attcgagatg agtttctgag gatcagcact    1020
gccagtggag atgggcgtca ctactgctac cctcatttca cctgcgctgt ggacactgag    1080
aacatccgcc gtgtgttcaa cgactgccgt gacatcattc agcgcatgca ccttcgtcag    1140
tacgagctgc tctaagaagg gaaccccaa  atttaattaa agccttaagc acaattaatt    1200
aaaagtgaaa cgtaattgta caagcagtta atcacccacc ataggcatg  attaacaaag    1260 caacctttcc cttcccccga gtgattttgc gaaaccccct tttcccttca gcttgcttag    1320
atgttccaaa tttagaaagc ttaaggcggc ctacagaaaa aggaaaaaag gccacaaaag    1380
ttccctctca ctttcagtaa aataaataa  aacagcagca gcaaacaaat aaaatgaaat    1440
aaaagaaaca aatgaaataa atattgtgtt gtgcagcatt aaaaaaatc  aaataaaaa     1500 ttaaatgtga gcaaag                                                    1516
```

<210> SEQ ID NO 3
<211> LENGTH: 1090
<212> TYPE: PRT
<213> ORGANISM: Rattus norvegicus

<400> SEQUENCE: 3

```
Met Arg Arg Arg Tyr Leu Arg Asp Arg Ala Glu Ala Ala Ala Ala
 1               5                  10                  15

Ala Ala Ala Gly Gly Gly Glu Gly Leu Gln Arg Ser Arg Asp Trp Leu
                20                  25                  30

Tyr Glu Ser Tyr Tyr Cys Met Ser Gln Gln His Pro Leu Ile Val Phe
                35                  40                  45

Leu Leu Leu Ile Val Met Gly Ala Cys Leu Ala Leu Leu Ala Val Phe
        50                  55                  60

Phe Ala Leu Gly Leu Glu Val Glu Asp His Val Ala Phe Leu Ile Thr
65                  70                  75                  80

Val Pro Thr Ala Leu Ala Ile Phe Phe Ala Ile Phe Ile Leu Val Cys
                85                  90                  95

Ile Glu Ser Val Phe Lys Lys Leu Leu Arg Val Phe Ser Leu Val Ile
                100                 105                 110

Trp Ile Cys Leu Val Ala Met Gly Tyr Leu Phe Met Cys Phe Gly Gly
        115                 120                 125

Thr Val Ser Ala Trp Asp Gln Val Ser Phe Phe Leu Phe Ile Ile Phe
130                 135                 140

Val Val Tyr Thr Met Leu Pro Phe Asn Met Arg Asp Ala Ile Ile Ala
145                 150                 155                 160

Ser Ile Leu Thr Ser Ser His Thr Ile Val Leu Ser Val Tyr Leu
                165                 170                 175

Ser Ala Thr Pro Gly Ala Lys Glu His Leu Phe Trp Gln Ile Leu Ala
                180                 185                 190

Asn Val Ile Ile Phe Ile Cys Gly Asn Leu Ala Gly Ala Tyr His Lys
        195                 200                 205

His Leu Met Glu Leu Ala Leu Gln Gln Thr Tyr Arg Asp Thr Cys Asn
        210                 215                 220

Cys Ile Lys Ser Arg Ile Lys Leu Glu Phe Glu Lys Arg Gln Gln Glu
225                 230                 235                 240

Arg Leu Leu Leu Ser Leu Leu Pro Ala His Ile Ala Met Glu Met Lys
                245                 250                 255

Ala Glu Ile Ile Gln Arg Leu Gln Gly Pro Lys Ala Gly Gln Met Glu
                260                 265                 270
```

```
Asn Thr Asn Asn Phe His Asn Leu Tyr Val Lys Arg His Thr Asn Val
            275                 280                 285

Ser Ile Leu Tyr Ala Asp Ile Val Gly Phe Thr Arg Leu Ala Ser Asp
            290                 295                 300

Cys Ser Pro Gly Glu Leu Val His Met Leu Asn Glu Leu Phe Gly Lys
305                 310                 315                 320

Phe Asp Gln Ile Ala Lys Glu Asn Glu Cys Met Arg Ile Lys Ile Leu
                325                 330                 335

Gly Asp Cys Tyr Tyr Cys Val Ser Gly Leu Pro Ile Ser Leu Pro Asn
            340                 345                 350

His Ala Lys Asn Cys Val Lys Met Gly Leu Asp Met Cys Glu Ala Ile
            355                 360                 365

Lys Lys Val Arg Asp Ala Thr Gly Val Asp Ile Asn Met Arg Val Gly
370                 375                 380

Val His Ser Gly Asn Val Leu Cys Gly Val Ile Gly Leu Gln Lys Trp
385                 390                 395                 400

Gln Tyr Asp Val Trp Ser His Asp Val Thr Leu Ala Asn His Met Glu
                405                 410                 415

Ala Gly Gly Val Pro Gly Arg Val His Ile Ser Ser Val Thr Leu Glu
            420                 425                 430

His Leu Asn Gly Ala Tyr Lys Val Glu Glu Gly Asp Gly Glu Ile Arg
            435                 440                 445

Asp Pro Tyr Leu Lys Gln His Leu Val Lys Thr Tyr Phe Val Ile Asn
            450                 455                 460

Pro Lys Gly Glu Arg Arg Ser Pro Gln His Leu Phe Arg Pro Arg His
465                 470                 475                 480

Thr Leu Asp Gly Ala Lys Met Arg Ala Ser Val Arg Met Thr Arg Tyr
                485                 490                 495

Leu Glu Ser Trp Gly Ala Ala Lys Pro Phe Ala His Leu His His Arg
            500                 505                 510

Asp Ser Met Thr Thr Glu Asn Gly Lys Ile Ser Thr Thr Asp Val Pro
            515                 520                 525

Met Gly Gln His Asn Phe Gln Asn Arg Thr Leu Arg Thr Lys Ser Gln
            530                 535                 540

Lys Lys Arg Phe Glu Glu Glu Leu Asn Glu Arg Met Ile Gln Ala Ile
545                 550                 555                 560

Asp Gly Ile Asn Ala Gln Lys Gln Trp Leu Lys Ser Glu Asp Ile Gln
                565                 570                 575

Arg Ile Ser Leu Leu Phe Tyr Asn Lys Asn Ile Glu Lys Glu Tyr Arg
            580                 585                 590

Ala Thr Ala Leu Pro Ala Phe Lys Tyr Tyr Val Thr Cys Ala Cys Leu
            595                 600                 605

Ile Phe Leu Cys Ile Phe Ile Val Gln Ile Leu Val Leu Pro Lys Thr
            610                 615                 620

Ser Ile Leu Gly Phe Ser Phe Gly Ala Ala Phe Leu Ser Leu Ile Phe
625                 630                 635                 640

Ile Leu Phe Val Cys Phe Ala Gly Gln Leu Leu Gln Cys Ser Lys Lys
                645                 650                 655

Ala Ser Thr Ser Leu Met Trp Leu Leu Lys Ser Ser Gly Ile Ile Ala
            660                 665                 670

Asn Arg Pro Trp Pro Arg Ile Ser Leu Thr Ile Val Thr Thr Ala Ile
            675                 680                 685
```

```
Ile Leu Thr Met Ala Val Phe Asn Met Phe Leu Ser Asn Ser Glu
    690             695             700
Glu Thr Thr Leu Pro Thr Ala Asn Thr Ser Asn Ala Asn Val Ser Val
705             710             715             720
Pro Asp Asn Gln Ala Ser Ile Leu His Ala Arg Asn Leu Phe Phe Leu
            725             730             735
Pro Tyr Phe Ile Tyr Ser Cys Ile Leu Gly Leu Ile Ser Cys Ser Val
        740             745             750
Phe Leu Arg Val Asn Tyr Glu Leu Lys Met Leu Ile Met Met Val Ala
    755             760             765
Leu Val Gly Tyr Asn Thr Ile Leu Leu His Thr His Ala His Val Leu
    770             775             780
Asp Ala Tyr Ser Gln Val Leu Phe Gln Arg Pro Gly Ile Trp Lys Asp
785             790             795             800
Leu Lys Thr Met Gly Ser Val Ser Leu Ser Ile Phe Phe Ile Thr Leu
            805             810             815
Leu Val Leu Gly Arg Gln Ser Glu Tyr Tyr Cys Arg Leu Asp Phe Leu
        820             825             830
Trp Lys Asn Lys Phe Lys Lys Glu Arg Glu Ile Glu Thr Met Glu
    835             840             845
Asn Leu Asn Arg Val Leu Leu Glu Asn Val Leu Pro Ala His Val Ala
    850             855             860
Glu His Phe Leu Ala Arg Ser Leu Lys Asn Glu Glu Leu Tyr His Gln
865             870             875             880
Ser Tyr Asp Cys Val Cys Val Met Phe Ala Ser Ile Pro Asp Phe Lys
            885             890             895
Glu Phe Tyr Thr Glu Ser Asp Val Asn Lys Glu Gly Leu Glu Cys Leu
        900             905             910
Arg Leu Leu Asn Glu Ile Ile Ala Asp Phe Asp Asp Leu Leu Ser Lys
    915             920             925
Pro Lys Phe Ser Gly Val Glu Lys Ile Lys Thr Ile Gly Ser Thr Tyr
    930             935             940
Met Ala Ala Thr Gly Leu Ser Ala Ile Pro Ser Gln Glu His Ala Gln
945             950             955             960
Glu Pro Glu Arg Gln Tyr Met His Ile Gly Thr Met Val Glu Phe Ala
            965             970             975
Tyr Ala Leu Val Gly Lys Leu Asp Ala Ile Asn Lys His Ser Phe Asn
        980             985             990
Asp Phe Lys Leu Arg Val Gly Ile Asn His Gly Pro Val Ile Ala Gly
    995             1000            1005
Val Ile Gly Ala Gln Lys Pro Gln Tyr Asp Ile Trp Gly Asn Thr Val
    1010            1015            1020
Asn Val Ala Ser Arg Met Asp Ser Thr Gly Val Leu Asp Lys Ile Gln
1025            1030            1035            1040
Val Thr Glu Glu Thr Ser Leu Ile Leu Gln Thr Leu Gly Tyr Thr Cys
            1045            1050            1055
Thr Cys Arg Gly Ile Ile Asn Val Lys Gly Lys Gly Asp Leu Lys Thr
        1060            1065            1070
Tyr Phe Val Asn Thr Glu Met Ser Arg Ser Leu Ser Gln Ser Asn Leu
    1075            1080            1085
Ala Ser
    1090
```

```
<210> SEQ ID NO 4
<211> LENGTH: 429
<212> TYPE: PRT
<213> ORGANISM: Homo sapiens

<400> SEQUENCE: 4

Met Trp Leu Leu Lys Ser Ser Gly Ile Ile Ala Asn Gln Pro Trp Pro
 1               5                  10                  15

Arg Ile Ser Leu Thr Ile Ile Thr Thr Ala Ile Ile Leu Met Met Ala
                20                  25                  30

Val Phe Asn Met Phe Phe Leu Ser Asp Ser Glu Glu Thr Ile Pro Pro
            35                  40                  45

Thr Ala Asn Thr Thr Asn Thr Ser Phe Ser Ala Ser Asn Asn Gln Val
        50                  55                  60

Ala Ile Leu Arg Ala Gln Asn Leu Phe Phe Leu Pro Tyr Phe Ile Tyr
65                  70                  75                  80

Ser Cys Ile Leu Gly Leu Ile Ser Cys Ser Val Phe Leu Arg Val Asn
                85                  90                  95

Tyr Glu Leu Lys Met Leu Ile Met Met Val Ala Leu Val Gly Tyr Asn
            100                 105                 110

Thr Ile Leu Leu His Thr His Ala His Val Leu Gly Asp Tyr Ser Gln
        115                 120                 125

Val Leu Phe Glu Arg Pro Gly Ile Trp Lys Asp Leu Lys Thr Met Gly
130                 135                 140

Ser Val Ser Leu Ser Ile Phe Phe Ile Thr Leu Leu Val Leu Gly Arg
145                 150                 155                 160

Gln Asn Glu Tyr Tyr Cys Arg Leu Asp Phe Leu Trp Lys Asn Lys Phe
                165                 170                 175

Lys Lys Glu Arg Glu Glu Ile Glu Thr Met Glu Asn Leu Asn Arg Val
            180                 185                 190

Leu Leu Glu Asn Val Leu Pro Ala His Val Ala Glu His Phe Leu Ala
        195                 200                 205

Arg Ser Leu Lys Asn Glu Glu Leu Tyr His Gln Ser Tyr Asp Cys Val
210                 215                 220

Cys Val Met Phe Ala Ser Ile Pro Asp Phe Lys Glu Phe Tyr Thr Glu
225                 230                 235                 240

Ser Asp Val Asn Lys Glu Gly Leu Glu Cys Leu Arg Leu Leu Asn Glu
                245                 250                 255

Ile Ile Ala Asp Phe Asp Asp Leu Leu Ser Lys Pro Lys Phe Ser Gly
            260                 265                 270

Val Glu Lys Ile Lys Thr Ile Gly Ser Thr Tyr Met Ala Ala Thr Gly
        275                 280                 285

Leu Ser Ala Val Pro Ser Gln Glu His Ser Gln Glu Pro Glu Arg Gln
290                 295                 300

Tyr Met His Ile Gly Thr Met Val Glu Phe Ala Phe Ala Leu Val Gly
305                 310                 315                 320

Lys Leu Asp Ala Ile Asn Lys His Ser Phe Asn Asp Phe Lys Leu Arg
                325                 330                 335

Val Gly Ile Asn His Gly Pro Val Ile Ala Gly Val Ile Gly Ala Gln
            340                 345                 350

Lys Pro Gln Tyr Asp Ile Trp Gly Asn Thr Val Asn Val Ala Ser Arg
        355                 360                 365

Met Asp Ser Thr Gly Val Leu Asp Lys Ile Gln Val Thr Glu Glu Thr
370                 375                 380
```

Ser Leu Val Leu Gln Thr Leu Gly Tyr Thr Cys Thr Cys Arg Gly Ile
385                 390                 395                 400

Ile Asn Val Lys Gly Lys Gly Asp Leu Lys Thr Tyr Phe Val Asn Thr
                405                 410                 415

Glu Met Ser Arg Ser Leu Ser Gln Ser Asn Val Ala Ser
            420                 425

<210> SEQ ID NO 5
<211> LENGTH: 4008
<212> TYPE: DNA
<213> ORGANISM: Rattus norvegicus

<400> SEQUENCE: 5

| | |
|---|---:|
| cccgggcagc gcgctctgcg gtcgcctacc gcctgccgcc ccgcgccgc cgcgacgtgg | 60 |
| caggaggcga tgcggcggcg ccgctacctg cgggaccgcg ccgaggcggc ggcggcagcg | 120 |
| gcggcgggag gcggagaggg gctgcagcgg tcccgggact ggctctacga gtcctactac | 180 |
| tgcatgagcc agcagcaccc gctcatcgtc ttcctgctgc tcatcgtcat gggcgcctgc | 240 |
| ctcgccctgc tagccgtctt cttcgcgctc gggctggagg tggaagacca tgtggcattt | 300 |
| ttaataacgg ttcccactgc cctggccatt ttctttgcca tattcattct tgtctgcata | 360 |
| gagtctgtgt tcaagaagct actccgtgtg ttttcgctgg tgatttggat atgtctggtt | 420 |
| gccatgggat acctgttcat gtgcttcgga gggactgtgt ctgcctggga ccaggtgtca | 480 |
| ttcttcctct tcatcatctt tgtggtatat accatgcttc ccttcaacat gcagatgcc | 540 |
| atcattgcca gcatcctcac atcttcatct catacgatag tgctgagcgt ctacctgtct | 600 |
| gcaacaccag gggccaagga gcacctgttc tggcagatac tggccaatgt gatcattttc | 660 |
| atttgtggga acttggcggg agcctaccac aagcacctca tggagcttgc cttgcagcaa | 720 |
| acctatcggg acacgtgtaa ttgcatcaag tcccggatca agctggaatt tgaaaaacgg | 780 |
| cagcaggaac ggctcctgct ctccttgctg ccagctcaca tcgccatgga gatgaaagct | 840 |
| gaaatcattc agaggctgca gggccccaaa gcaggacaga tggaaaacac aaacaacttc | 900 |
| cacaatctgt atgtcaaacg acacaccaac gtgagcatat tatacgctga cattgttggc | 960 |
| ttcacccgcc ttgcaagcga ttgctcccct ggcgaactgg tccacatgct gaatgaactc | 1020 |
| tttgggaagt tgatcaaat agcaaaggag aatgaatgca tgagaattaa aattttagga | 1080 |
| gactgctatt actgtgtttc cgggctccct atatcactcc ctaaccatgc caagaactgt | 1140 |
| gtgaaaatgg gattggatat gtgcgaagcc ataaagaaag tgagggatgc taccggagtt | 1200 |
| gatatcaaca tgcgtgtagg agtgcattct gggaacgttc tctgtggtgt gattggtctc | 1260 |
| cagaagtggc agtatgatgt gtggtctcat gatgttactc tggcaaacca catggaagct | 1320 |
| ggaggagtcc ctgggcgtgt tcacatttct tcagtcactc tggagcactt gaatgggct | 1380 |
| tataaagtgg aggaaggaga tggtgagata agagacccat atttaaagca gcacttggtg | 1440 |
| aaaacctact tgtaatcaa tcccaaggga gagcgacgga gtcctcagca tctcttcaga | 1500 |
| cctcgacaca ctctggacgg agccaagatg agagcatctg tccgcatgac ccggtacttg | 1560 |
| gagtcctggg gagcagccaa gccattcgca catctgcacc acagagatag catgaccaca | 1620 |
| gagaatggga agattagtac cacgatgtg ccaatgggtc aacataattt tcaaaatcgc | 1680 |
| accttaagaa ctaagtcaca gaagaagaga tttgaagaag aactgaatga aggatgatc | 1740 |
| caagcaattg atgggatcaa tgcacagaag caatggctca gtcagaaga cattcaaaga | 1800 |
| atctccctgc ttttctataa caagaatata gagaaagaat accgagctac tgcactgcca | 1860 |

```
gcattcaagt actacgtgac ctgtgcctgc ctcatctttc tctgcatctt cattgtacag    1920
atacttgtat tgccaaaaac gtccatcctt ggcttctcct ttggagctgc atttctctcc    1980
ctcatcttca tcctctttgt ctgcttcgct ggacagcttt tgcaatgcag caaaaaggcc    2040
tccacctctc tcatgtggct tttgaaatca tcaggcatca tcgccaaccg cccatggcca    2100
cggatctccc tcacaatcgt caccacggct atcatactaa ccatggctgt gttcaacatg    2160
tttttcctga gcaactctga ggagacaacc cttcccactg ccaatacatc aaatgcaaac    2220
gtttctgtcc cggataacca ggcgtcgatt cttcatgctc gaaacttgtt tttcctcccg    2280
tacttcatat acagctgcat cctgggcttg atctcctgct ccgttttcct gagggtgaac    2340
tatgagttaa aaatgttaat catgatggtg gcactcgtgg gctacaacac cattctactc    2400
cacacccatg cccatgttct ggatgcgtac agccaggtcc tgtttcagag accaggcatt    2460
tggaaagacc tgaagaccat gggctccgtg tcactctcca tattcttcat cacgctgctg    2520
gttctgggca gacagagtga atattactgt aggttagact tcttgtggaa gaacaagttc    2580 aaaaagagc gggaggagat agaaaccatg gagaacctaa atcgagtgct gctggagaac    2640
gtgcttcctg cacacgtggc tgaacacttc ctggccagga gcctgaaaaa tgaggagctg    2700
taccaccagt cctacgactg tgtctgtgtc atgtttgcct ccattccgga cttcaaggag    2760
ttctacacag agtcagatgt gaacaaggaa ggcttggaat gcctgcggct cctgaatgag    2820
atcattgctg actttgatga tctgcttttct aagccaaagt tcagtggtgt tgaaaagatc    2880
aagaccattg ggagcacata catggcagcc acgggactga gtgccatacc cagccaggag    2940
cacgcccagg aacctgagcg tcagtacatg cacataggca ccatggtgga gtttgcatat    3000
gccctggtgg gaaaactgga tgccatcaat aagcactcct caacgactt caaactgcga    3060 gtgggtatca accatgggcc tgtaatagct ggcgtcatag gggctcaaaa gccacagtat    3120
gacatctggg gcaacactgt caacgtggcc agcagaatgg acagcaccgg ggtcctggac    3180
aaaatacagg tgactgagga gacaagcctc atcttgcaga cgcttggcta cacgtgtaca    3240
tgtcgaggta tcatcaatgt gaaggggaaa ggggacctga agcatatatt tgtaaacaca    3300
gagatgtcaa ggtcccttttc tcagagcaac ttggcatcct gagaagctgt ctcttcctga    3360
caagaagaat gtacttgcag gaaggtacca cgcactttct gactgcaacc cttcccccttc    3420 gtcctgatgt acgtgctctg ccccatcctc tggagcccct gcagactagt tcctgtgacc    3480
cagtgacata ctgtttggtg tctgcgcgtg cccaggttgt cctgccactt gcactgtgct    3540
tgctcctaag caggaggggga aggaaccatg tcctggaagg agagcattgg aagaagtgat    3600
gaagaggtga agtgaacaca cattcttaag gcaataaaac cgggggggtgt atattatctt    3660 ctggtgcatg ttcttctctg gaaaatacgg tagctcgtaa ctgcatccct agtctgatat    3720
tcaaacacac agtatttgtg aataagctga tcccgtcacc caacatggag tctgtgttca    3780
cctacccatg tgtctcattg ccagtggtcg tccttggggg ctcagctgag actctcagct    3840
tctgtcacct tgctgtcctg tcttgtggca gcagcacgtt gccatccatc accagaatta    3900
gtcctcacag cctaggacca gttttgtacc aaactcatct gatgttttga tgccatttgt    3960
caaaagtaag gttaattcat taaaagttttt atgtactttg aaaaaaaa                4008
```

<210> SEQ ID NO 6
<211> LENGTH: 2092
<212> TYPE: DNA
<213> ORGANISM: Homo sapiens

<400> SEQUENCE: 6

```
attgtgcaga ttctcgtgct gccaaaaacg tctgtcctgg gcatctcctt tggggctgcg      60
tttctcttgc tggccttcat cctcttcgtc tgctttgctg acagcttct gcaatgcagc     120
aaaaaagcct ctcccctgct catgtggctt ttgaagtcct cgggcatcat tgccaaccag    180
ccctggccac ggatctctct cacgatcatc accacagcca tcatattaat gatggccgtg    240
ttcaacatgt ttttcctgag tgactcagag gaaacaatcc ctccaactgc caacacaaca    300
aacacaagct tttcagcctc aaataatcag gtggcgattc tgcgtgcgca gaatttattt    360
ttcctcccgt actttatcta cagctgcatt ctgggactga tatcctgttc cgtgttcctg    420
cgggtaaact atgagctgaa gatgttgatc atgatggtgg ccttggtggg ctacaacacc    480
atcctactcc acacccacgc ccacgtcctg gcgactaca gccaggtctt atttgagaga    540
ccaggcattt ggaaagacct gaagaccatg ggctctgtgt ctctctctat attcttcatc    600
acactgcttg ttctgggtag acagaatgaa tattactgta ggttagactt cttatggaag    660
aacaaattca aaaagagcg ggaggagata gagaccatgg agaacctgaa ccgcgtgctg     720
ctggagaacg tgcttcccgc gcacgtggct gagcacttcc tggccaggag cctgaagaat    780
gaggagctat accaccagtc ctatgactgc gtctgcgtca tgtttgcctc cattccggat    840
ttcaaagaat tttatacaga atccgacgtg aacaaggagg gcttggaatg ccttcggctc    900
ctgaacgaga tcatcgctga ctttgatgat cttctttcca agccaaaatt cagtggagtt    960
gaaaagatta gaccattgg cagcacatac atggcagcaa caggtctgag cgctgtgccc    1020
agccaggagc actcccagga gcccgagcgg cagtacatgc acattggcac catggtggag    1080
tttgcttttg ccctggtagg gaagctggat gccatcaaca gcactccttc aacgacttc    1140
aaattgcgag tgggtattaa ccatggacct gtgatagctg gtgtgattgg agctcagaag    1200
ccacaatatg atatctgggg caacactgtc aatgtggcca gtaggatgga cagcaccgga    1260
gtcctggaca aaatacaggt taccgaggag acgagcctcg tcctgcagac cctcggatac    1320
acgtgcacct gtcgaggaat aatcaacgtg aaaggaaagg gggacctgaa gacgtacttt    1380
gtaaacacag aaatgtcaag gtcccttttcc cagagcaacg tggcatcctg aagagtcacc    1440
ttcattttgg caagaagact gtattttcag gaaggtatca cacactttct gactgcaact    1500
tctgtccctt gtttttgatg tgcgtgctgt ctgtcctatg gagcctctgc agactcgttc    1560
tcgtgaccca gtggcatacc gtttggtgtc tgatgtgtgc ccagatcgtt ctgccacttg    1620
cactgtgctt gctcctaagc aaaagggaaa aggagcgcgc gtgatagaag aaaagcactg    1680
ggagaactaa cagaggagaa aggtgaaaca cacacacatt cttaaggcaa taaaactagg    1740
gggtgtatat tatcttctgg tgcatgttct ttctggaaa atatggtagc tcgccaaccg    1800
catctgctca tctgatattc aaacacacag tattcgtgaa taagttgatt ctgtccccca    1860
cgtggactct gtgctcaccc attgtctcat tgccagtggt gtccaaggc ccccgttggg    1920
acccacggct ctcgtccctc tgctccgtgt gtctcatgcc agcagcacgt cgccatccgt    1980
caccagaatt agtcctcaca gcctaggacc agttttgtat caaactcgtc tgatgttttg    2040
atgccatttg tcttttgtaa agttaattca ttaaaagttt tatgtacttt ga            2092
```

<210> SEQ ID NO 7  
<211> LENGTH: 14  
<212> TYPE: PRT  
<213> ORGANISM: Artificial Sequence  
<220> FEATURE:  
<223> OTHER INFORMATION: Peptide sequence

```
<400> SEQUENCE: 7

Ile Gly Ala Arg Lys Pro Gln Tyr Asp Ile Trp Gly Asn Thr
1               5                   10

<210> SEQ ID NO 8
<211> LENGTH: 56
<212> TYPE: DNA
<213> ORGANISM: Artificial Sequence
<220> FEATURE:
<223> OTHER INFORMATION: AC2 CDNA was excised from pBSII-AC2 and
                         inserted into pVL-1392

<400> SEQUENCE: 8
tacaagcggc cgcatggact acaaggacga cgacgataag cggcggcgcc gctacc          56

<210> SEQ ID NO 9
<211> LENGTH: 8
<212> TYPE: PRT
<213> ORGANISM: Artificial Sequence
<220> FEATURE:
<223> OTHER INFORMATION: Peptide sequence

<400> SEQUENCE: 9

Asp Tyr Lys Asp Asp Asp Asp Lys
1               5
```

MUTANT ACTIVATED $G_s\alpha$ AND ADENYLYL CYCLASE 2 FOR USE AS THERAPEUTIC AGENTS This invention was made with government support under grand number CA-44998 awarded by the National Institutes of Health. The government has certain rights in the invention.

1. INTRODUCTION

The present invention relates to therapeutic uses of mutant activated $G_s\alpha$ and adenylyl cyclase 2. It is based, at least in part, on the discoveries that (1) the expression of mutant activated $G_s\alpha$ suppresses proliferation and the expression of the transformed phenotype in certain cells and (2) adenylyl cyclase 2 is specifically activated and modified by protein kinase C, thereby permitting tissue-selective increases in cyclic adenosine monophosphate ("cAMP") levels by growth factors and other proliferative agents that stimulate the protein kinase C pathway.

2. BACKGROUND OF THE INVENTION

The cAMP signal transducing system comprises a number of proteins embedded in the plasma membrane, including an adenylyl cyclase catalyst, cell-surface receptors, and a pair of homologous guanine nucleotide binding (so-called "G") proteins (Levine, 1991, N. Engl. J. Med. 325: 1738–1740; Gilman, 1987, Ann. Rev. Biochem. 56: 615–649). One of the G proteins, termed $G_s$, couples stimulatory receptors to the activation of adenylyl cyclase (Levine, 1991, N. Engl. J. Med. 325: 1738–1740). The other, termed $G_i$, effects inhibition of enzyme activity through inhibitory receptors (Id.). The $G_s$ and $G_i$ proteins are members of a superfamily of signal-transducing proteins that mediate numerous transmembrane hormone and sensory processes (Id.).

G proteins share a heterotrimeric structure comprising $\alpha$, $\beta$ and $\gamma$ subunits, each the product of a separate gene (Weinstein et al., 1991, N. Engl. J. Med. 325: 1688–1695). The $\beta$ and $\gamma$ subunits are tightly associated with each other, and appear to be structurally interchangeable (Levine, 1991, N. Engl. J. Med. 325: 1738–1740). The $\alpha$ subunit contains a guanine nucleotide binding site and has intrinsic guanosine triphosphatase ("GTPase") activity (Id.). Functional specificity of G proteins is thought to derive from the identity of their $\alpha$ subunits, which exhibit the greatest structural diversity, allowing discrimination among multiple receptors and effector molecules (Id.).

Signal transduction begins by the binding of a stimulatory hormone, neurotransmitter, or drug to its receptor(Id.). The activated receptor then interacts with $G_s$, causing it to release guanosine diphosphate ("GDP") and thereby allow the binding of guanosine triphosphate ("GTP") to its guanine nucleotide binding site (Id.). This binding triggers the dissociation of the $\alpha$ chain from the hetero-trimer. The released $G_s\alpha$ protein stimulates adenylyl cyclase activity and thereby increases the synthesis of cAMP, which, in turn, stimulates a physiological response via protein kinase A ("PKA"; Id.). Finally, the bound GTP is hydrolysed to GDP, promoting the reassociation of the $\alpha$, $\beta$ and $\gamma$ subunits, which restores $G_s\alpha$ to an inactive state (Id.).

2.1. ADENYLYL CYCLASE

Adenylyl cyclase exists as multiple molecular species (Iyengar R. (1993) FASEB J. 7:768–775). At least six $G_s$-stimulated adenylyl cyclases have been cloned (Pieroni et al., 1993, Curr. Opin. Neurobiol. 3: 345–351).

The first mammalian adenylyl cyclase gene to be cloned was the gene encoding the $Ca^{2+}$/calmodulin ("CaM")-sensitive form from bovine brain (Krupinski et al., 1989, Science 244: 1558–1564; Gilman, 1987, Ann. Rev. Biochem. 56: 615–649, citing Salter et al., 1981, J. Biol. Chem. 256: 9830–9833; Andreasen et al., 1983, Biochemistry 22: 2757–2762; and Smigel et al., 1986, J. Biol. Chem. 261: 1976–1982), termed adenylyl cyclase, type 1 ("AC 1"). Using probes derived from this sequence, five additional full-length cDNAs encoding different adenylyl cyclases have been cloned. These are type 2 ("AC 2"; Feinstein et al., 1991, Proc. Natl. Acad. Sci. U.S.A. 88: 10173–10177), type 3 ("AC 3"; Bakalyar and Reed, 1990, Science 250: 1403–1406), type 4 ("AC 4"; Gao and Gilman, 1991, Proc. Natl. Acad. Sci. U.S.A. 88: 10178–10182), type 5 ("AC 5"; Ishikawa et al., 1992, J. Biol. Chem. 267: 13553–13557; Premont et al., 1992, Proc. Natl. Acad. Sci. U.S.A. 89: 9809–9813; Glatt and Snyder, 1993, Nature 361:536–538), and type 6 ("AC 6"Premont et al., 1992, Proc. Natl. Acad. Sci. U.S.A. 89: 9809–9813; Yoshimura and Cooper, 1992, Proc. Natl. Acad. Sci. U.S.A. 89: 6716–6720; Katsushika et al., 1992, Proc. Natl. Acad. Sci. U.S.A. 89: 8774–8778; Krupinski et al., 1992, J. Biol. Chem. 267: 24858–24862). Two partial sequences encoding type 7 ("AC 7"; Krupinski et al., 1992, J. Biol. Chem. 267: 24858–24862) and type 8 ("AC 8"; Krupinski et al., 1992, J. Biol. Chem. 267: 24858–24862; Parma et al., 1991, Biochem. Biophys. Res. Commun. 179: 455–462) have also been identified.

Localization studies using mRNA probes have been used to determine tissue distribution of the various adenylyl cyclases (Pieroni et al., 1993, Curr. Opin. Neurobiol. 3: 345–351). AC 1 appears to be present only in neuronal tissue, whereas AC 2 has been found in brain and lung. AC 3 has been localized in olfactory neurons as well as other neuronal and non-neuronal tissues (Glatt and Snyder, 1993, Nature 361: 536–538; Xia et al., 1992, Neurosci. Lett. 144: 169–173). AC 4 appears to be present at very low levels in brain, and throughout most tissues. AC 5 and AC 6 have also been found to be widely distributed (Premont et al., 1992, Proc. Natl. Acad. Sci. U.S.A. 89: 9809–9813; Krupinski et al., 1992, J. Biol. Chem. 267: 24858–24862) although AC 6 seems to be of very low abundance in the brain. AC 5 is particularly abundant in the heart and in some regions of the brain. AC 7 appears to be widely distributed, but may be scarce in the brain. AC 8, like AC 1, seems to be abundant in the brain. Within the brain, the distributions of AC 1, AC 2, AC 3, AC 5 and AC 8 show distinct regional patterns.

With the cloning and characterization of multiple forms of adenylyl cyclases (Iyengar, 1993, FASEB J. 7:768–775) has come the recognition that different isoforms of adenylyl cyclase can have different signal recognition capabilities. One example is the ability of AC 2 to be stimulated by the activation of protein kinase C (Jacobowitz et al., 1993, J. Biol. Chem. 268:3829–3832; Yoshimura and Cooper, 1993, J. Biol. Chem. 268: 4604–4607; Lustig et al., 1993, J. Biol. Chem. 268: 13900–13905). It had been known for some time that in some cells and tissues cAMP production could be stimulated by the activation of protein kinase C (Bell et al., 1985, J. Biol. Chem. 260: 2625–2628; Sibely et al., 1986, Arch. Biochem. Biophys. 244:373–381; Rozengurt et al., 1987, Proc. Natl. Acad. Sci. U.S.A. 84:2282–2286; Naghshineh et al., 1986, J. Biol. Chem. 261: 14534–14538). Some suggested that such regulation may occur at the level of the G protein (Katada et al., 1985, Eur. J. Biochem. 151:431–437; Bushfield et al., 1990, Biochem. J. 268:449–457) while others viewed adenylyl cyclase as the target of regulation (Yoshimasa et al., 1987, Nature 327:

67–70; Simmoteit et al., 1991, FEBS 285: 99–103). Using transient expression in mammalian cells, it was demonstrated that AC 2 (but not other isoforms of adenylyl cyclase) was extensively stimulated by activation of protein kinase C (Jacobowitz et al., 1993, J. Biol. Chem. 268:3829–3832; Yoshimura and Cooper, 1993, J. Biol. Chem. 268: 4604–4607).

Regulation of AC 2 enzyme by protein kinase C shows several interesting features. The first is that protein kinase C has its greatest effect on the basal activity of the type 2 enzyme. In broken-cell adenylyl cyclase assays a three- to five-fold increase in the basal activity of AC 2 was observed (Jacobowitz et al., 1993, J. Biol. Chem. 268: 3829–3832). Using an intact-cell cAMP assay, Yoshimura and Cooper (1993, J. Biol. Chem. 268: 4604–4607) reported that protein kinase C produces nearly a ten-fold increase in AC 2 activity. A second interesting feature is that protein kinase C treatment selectively abolishes $G_i\alpha$-induced inhibition of AC 2, but does not affect the inhibition of AC 3 and AC 6 (Chen and Iyengar, 1993, J. Biol. Chem. 268: 12253–12256). Third, AC 2 can be stimulated via receptors that activate phospholipases, without activation of the $G_s$ system (Iyengar, 1993, FASEB J. 7: 768–775).

A schematic diagram of signalling pathways that can regulate the activity of the $G_s$-sensitive adenylyl cyclases is presented in FIG. 1 (Pieroni et al., 1993, Curr. Opin. Neurobiol. 3: 345–351). This diagram shows that AC 2 can raise the cellular cAMP concentration in response to a variety of signals. In cells in which AC 2 is the most abundant species of adenylyl cyclase, increases in cellular cAMP can be achieved through receptors that activate $G_s$, $G_i$, $G_o$, and phospholipases (Id.). As phospholipases can be either G protein coupled or G protein independent, AC 2 may raise intracellular cAMP in response to an even larger set of signals, including the G protein independent growth factors that activate phospholipase C-γ.

For example, in PC12 cells, nerve growth factor stimulates phosphorylation of phospholipase C-γ (Kim et al., 1991, J. Biol. Chem. 266: 1359–1362) and raises intracellular levels of cAMP (Shubert and Whitlock, 1975, Proc. Natl. Acad. Sci. U.S.A. 74: 4055–4058). Although it is not known whether this nerve growth factor stimulated increase in cAMP is mediated through protein kinase C effects on AC 2, this would be a feasible mechanistic explanation. If this is, indeed, the case, then the limited distribution of AC 2 in certain neuronal cells may explain why nerve growth factor-induced increases in the levels of cAMP are not always observed.

Further, the βγ subunits released from the more abundant G proteins, such as $G_i$ and $G_s$, also will enhance the $G_s\alpha$ signal; thus, AC 2 can integrate signals from multiple G protein pathways. Such integration has, in fact, been observed both at the level of cAMP accumulation (Sattin et al., 1975, J. Pharmacol. Exp. Ther. 192: 22–32; Karbon et al., 1985, Mol. Pharmacol. 27: 53–59; Federman et al., 1992, Nature 356: 159–161) and cAMP-dependent electrophysiological responses (Andrade, 1993, Neuron 10: 83–88).

The abolishment of $G_{i\alpha}$-induced inhibition by protein kinase C is a unique feature of AC 2 (Pieroni et al., 1993, Curr. Opin. Neurobiol. 3: 345–351). Of the known signalling molecules, only $G_{i\alpha}$ is capable of inhibiting AC 2, all the others stimulate it. As even this inhibition can be suppressed by other signals (i.e., via protein kinase C), the primary role of AC 2 may be to raise cellular levels of cAMP in response to numerous signals.

2.2. EFFECTS OF MUTATION OF $G_s\alpha$

The fact that cAMP serves as an intracellular second messenger for several trophic hormones, as well as its ability to stimulate the growth of certain cultured cells, suggest that mutations in genes encoding proteins that increase cAMP synthesis, such as the G proteins, may be oncogenic (Landis et al., 1989, Nature 340: 692–696). However, such mutations would not be expected to be oncogenic in all tissues, because cells programmed to proliferate in response to increased cAMP levels represent a relatively small subset of differentiated cells, including certain endocrine cells (e.g., ovary, adrenal cortex, thyroid, and some cells of the pituitary (Landis et al., 1989, Nature 340: 692–696, citing Dumont et al., 1989, Trends Biochem. Sci. 14: 67–71 and Rozengurt, 1986, Science 234: 161–166)), melanocytes and osteoblasts (Weinstein et al., 1991, N. Engl. J. Med. 325: 1688–1695).

Landis et al., 1989, Nature 340:692–696, have identified mutations in $G_s\alpha$ that cause autonomous cAMP synthesis in four growth hormone-secreting pituitary tumors. These mutations, which occur at codons 201 and 227, appear to cause constitutive activation of $G_s\alpha$ by inhibiting its GTPase activity. Replacement of the $Arg^{201}$ residue with cysteine or histidine was associated with a 30-fold decrease in intrinsic GTPase activity, and cell membranes containing such mutant $G_s\alpha$ were observed to produce cAMP at an elevated rate in the absence of any stimulatory hormone (Id.). Similarly, replacement of Glu 227 by other amino acid residues also has been shown to result in a large decrease in GTPase activity (Bourne et al., 1991, Nature 350:117).

In another example of constitutive activation of $G_s\alpha$, an adenosine diphosphate-ribose group is added to the arginine residue at position 201 by the exotoxin of Vibrio cholerae (Weinstein et al., 1991, N. Engl. J. Med. 325: 1688–1695, citing Birnbaumer et al., 1990, Biochem. Biophys. Acta 1031: 163–224). Targeted expression of the catalytic subunit of cholera toxin in transgenic mice has been found to result in pituitary somatotroph hyperplasia and gigantism, presumably through the constitutive activation of $G_s\alpha$ (Weinstein et al., 1991, N. Engl. J. Med. 325:1688–1695, citing Burton et al., 1991, Nature 350: 74–77).

Interestingly, an association has been drawn between activating mutations of $G_s\alpha$ and McCune-Albright syndrome, an unusual clinical condition characterized by a triad of bone, skin, and endocrine abnormalities (Weinstein et al., 1991, N. Engl. J. Med. 325: 1688–1695; Levine, 1991, N. Engl. J. Med. 325: 1738–1740). However, the presence of $G_s\alpha$ mutations in pancreas, kidney, and blood was not associated with clinical abnormalities in one study of patients suffering from McCune-Albright syndrome (Weinstein et al., 1991, N. Engl. J. Med. 325: 1688–1695).

2.3. RELATIONSHIP TO RAS PATHWAYS

Ras functions as a downstream element of several growth factor receptor tyrosine kinases (Lowy and Willumsen, 1993, Ann. Rev. Biochem. 62: 851). Both Ras and $G_s\alpha$ belong to the GTPase superfamily and can be converted to their active forms by mutations that block their intrinsic GTPase activities (Bourne et al., 1991, Nature 349: 117).

Mutant forms of Ras have been identified in a wide variety of human tumors (Egan and Weinberg, 1993, Nature 365: 781–783, citing Bos, 1989, Cancer Res. 49: 4682–4689). Such oncogenic forms of Ras have greatly reduced GTPase activity and therefore remain active for extended periods, flooding the cell with growth stimulatory signals (Egan and Weinberg, 1993, Nature 365: 781–783).

It has recently been discovered that many other oncoproteins participate in an evolutionarily conserved signalling pathway featuring Ras as a central element (Id., for review). This pathway begins at the cell surface, where a growth factor (e.g., epidermal growth factor) binds to its tyrosine kinase receptor, resulting in autophosphorylation of the receptor's tyrosine residues. Next, controllers of Ras exchange factors, such as Grb2/Sem5, recruit exchange factors (or activators, such as Sos), to interact with Ras. The activators, in turn, function as guanine-nucleotide releasing agents which convert (inactive) Ras-GDP to (active) Ras-GTP. Ras-GTP recruits to the cell surface and activates Raf protein, another oncoprotein. Activated Raf phosphorylates MAP kinase kinase ("MEK", which, via still other kinases (including MAP kinase) pass signals triggering proliferation to the nucleus by phosphorylating transcription factors that directly regulate gene expression.

There is "cross-talk" between the above-outlined Ras/MAP-kinase signalling pathway and other pathways, including those that utilize the second messenger cAMP. For example, it has been shown that protein kinase C-α efficiently phosphorylates and activates the Raf protein (Egan and Weinberg, 1993, Nature 365: 781–783).

On the other hand, some effects mediated by cAMP and protein kinase A are known to be in the opposite direction compared to effects stimulated by growth factors having protein tyrosine kinase receptors. For example, whereas stimulation of aortic smooth muscle cells with platelet-derived growth factor BB homodimer (PDGF-BB) leads to rapid activation of mitogen-activated protein kinase (MAPK) and MAPK kinase (MEK), compounds that increase cAMP and activate protein kinase A, such as prostaglandin $E_2$, isoproterenol, cholera toxin, and forskolin, were found to inhibit PDGF-induced activation of MAPK and MEK (Graves et al., 1993, Proc. Natl. Acad. Sci. U.S.A. 90:10300–10304). Increasing intracellular concentrations of cAMP has been shown to inhibit proliferation of such vascular smooth muscle cells (Assender et. al. 1992 Biochem J.288: 527–532).

2.4. ONCOGENES AND BREAST CANCER

A relationship has been drawn between activation of oncogenes and breast cancer. For example, it has been reported that tyrosine kinase activity (associated with many oncogenes) of cytosolic and membrane fractions of malignant breast tissue was significantly higher compared to the activity levels present in benign or normal breast tissue (Hennipman et al., 1989, Cancer Res. 49: 516–521). In another study (Ottenhoff-Kalff et al., 1992, Cancer Res. 52:4773–4778), when the protein tyrosine kinase activity of 72 breast cancer specimens was measured, the level of activity in all 72 tumors was found to be higher than normal controls; at least 70% of the cytosolic activity was observed to originate from the presence of the c-src oncogene product.

Moreover, the expression of c-erbB-2 encoded protein (which is closely related in structure to the epidermal growth factor receptor) was found to be over-expressed in about 20% of human breast cancers (Gullick et al., 1991, Br. J. Cancer 63: 438). It has been suggested that amplification of c-erbB-2 may contribute to the pathogenesis of some forms of node-negative breast cancer and may serve as a useful genetic marker to identify a subset of high-risk patients (Paterson et al., 1991, Cancer Res. 51: 556–567). Further, it has been observed that as breast tumors become aggressive and refractory to treatment with antiestrogens, they acquire EGF receptors (Nicholson et. al., 1989, Lancet 1:182–184).

3. SUMMARY OF THE INVENTION

The present invention relates to therapeutic uses of mutant activated $G_s\alpha$ and adenylyl cyclase 2. Although mutant activated $G_s\alpha$ has been, previously, associated with proliferative disorders of a subset of differentiated cells, it has now been discovered that mutant activated $G_s\alpha$ (referred to, hereafter, as $G_s\alpha^*$) can suppress proliferation as well as the transformed phenotype.

Accordingly, in various embodiments of the present invention, $G_s\alpha^*$ may be introduced into a cell in order to reduce proliferation and/or prevent the development of, reduce, or reverse malignancy. In specific, non-limiting embodiments of the invention, DNA encoding $G_s\alpha^*$ may be introduced into a malignant cell, such as a breast cancer cell, in order to decrease the malignant phenotype of that cell.

In additional embodiments, the methods of the present invention may be used to limit cell proliferation where such proliferation may be undesirable. For example, the introduction of $G_s\alpha^*$ may be used to limit the proliferation of coronary artery smooth muscle cells following angioplasty, where such proliferation is associated with artery restenosis.

In still further embodiments of the present invention, the introduction of adenylyl cyclase 2 may be used to limit cell proliferation and/or reduce the transformed phenotype. Because adenylyl cyclase 2 is not endogenous to most tissues but can be activated by growth factors and other agents that stimulate proliferation in a subset of malignant or otherwise proliferative cells (i.e., those that stimulate phospholipases C or D), the introduction of adenylyl cyclase 2 may be used to selectively increase CAMP levels and thereby prevent, reduce, or reverse proliferation and/or malignancy.

4. DESCRIPTION OF THE FIGURES

FIG. 1. A schematic diagram of signalling pathways that can regulate the activity of $G_s$-sensitive adenylyl cyclases. Pathways to and from the βγ subunits are shaded. RTK, receptor tyrosine kinase; PLC, phospholipase C; PKC, protein kinase C; PKA, cAMP-dependent protein kinase.

Figure 2B:
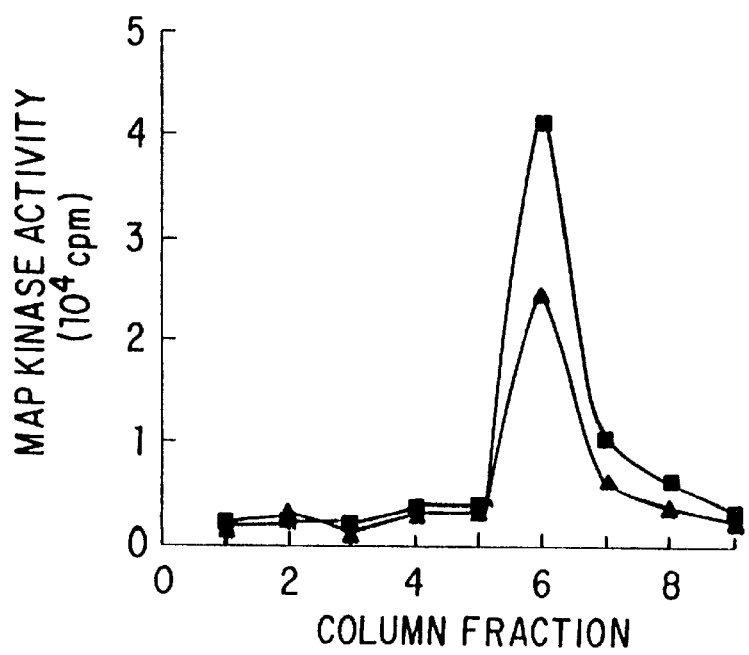
Figure 2C:
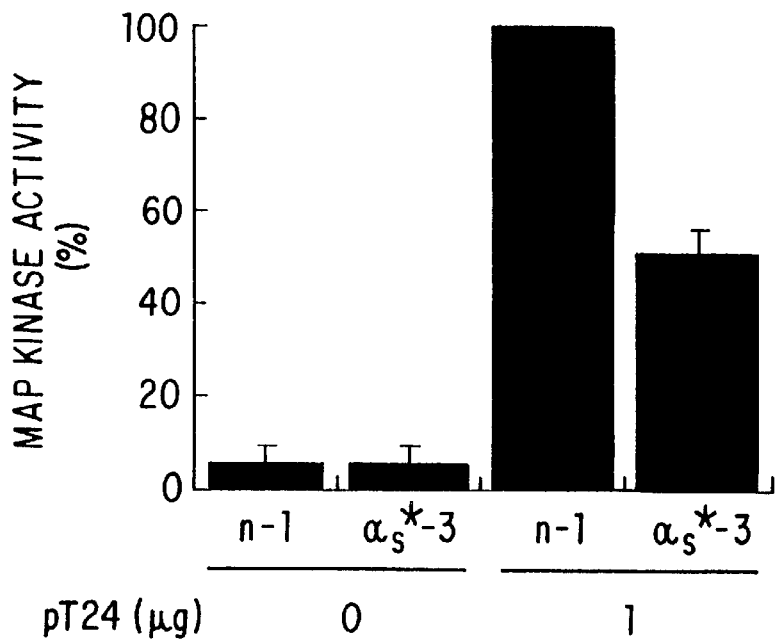

FIG. 2. Effects of expression of mutant activated $G_s\alpha$ on H-Ras-induced mutagenesis (A) and MAP kinase activity (B and C). Clonal NIH 3T3 lines n–1 and $\alpha_s^*$ –3 were derived from cells transfected with pMAM-neo and pMAM-neo-$\alpha_s^*$, respectively. The $a_s^*$ –3 line expressed $\alpha_s^*$ when treated with dexamethasone. These cell lines were transfected with or without pT24, an H-ras-containing plasmid, and cultured for two weeks, with dexamethasone added on alternate days. The cells were split on every third day. After the two week period, the cells were plated in 24-well plates and incorporation of [$^3$H]thymidine was measured. (A) Values are means of triplicate determinations. The results of one representative of four experiments are shown. (B and C) Cells ($4\times10^6$ per 100-mm plate) were incubated for 20 hours with DMEM without serum but with bovine serum albumin (0.1%) to achieve quiescence. The cells were then extracted and MAP kinase activity was measured. (B) Column profiles of H-Ras-stimulated MAP kinase activity (in a 0.20 microliter portion of column eluate) from control (solid square) and $\alpha_s^*$-expressing (solid triangle) clonal lines in one experiment. (C) A summary of four separate experiments. Values are means ± SD.

FIG. 3. Effects of $\alpha_s^*$ on H-Ras-induced transformation of NIH 3T3 cells. (a) Soft agar plates of cells from the clonal lines n–1 and $\alpha_s^*$–3 transfected with the indicated amounts of H-ras plasmid pT24 by the calcium phosphate method. The transfected cells were treated with 1 micromolar dexamethasone to induce expression of $\alpha_s^*$, and then plated onto soft agar to assess colony formation. (B) Immunoprecipitation of Ras proteins extracted from NIH 3T3 cell lines, n-1 and $a_s^*-3$, that were cotransfected with 20 micrograms of genomic NIH 3T3 DNA and 1 microgram pRSV 1.1, with or without 5 micrograms H-ras plasmid. The cells were cultured, labelled, and extracted, and Ras was immunoprecipitated. (C) Several NIH 3T3 cell lines were transfected with various amounts of H-ras plasmid as indicated. The ability of transfected cells to form colonies in soft agar was determined. NIH 3T3 lines used were (1) n-1, a control vector-containing cell line (solid bars); (2) $\alpha_s$-2, a cell line expressing exogenous wild-type $G_s\alpha$ ([/] bars); (3) $\alpha_s^*-3$, expressing mutant activated $G_s\alpha$ ([\] bars) and (4) $\alpha_s^*-14$, expressing mutant activated $G_s\alpha$ (open bars). Values are means ± SD of triplicate plates. The experiment depicted in each panel is representative of three experiments except for the immunoblotting, which was done only twice.

FIG. 4. Effects of 8-Br-cAMP on mitogenesis and H-Ras-induced transformation of Rat-1 and NIH 3T3 lines. (A) Cells were seeded into 24 well plates ($1\times10^3$ cells per well) in 1 ml. DMEM with 10% bovine calf serum in either the presence (open squares) or absence (solid squares) of 1 micromolar 8-Br-cAMP. Each group consisted of four wells. The number of cells was determined on days 3, 4 and 5. Doubling times were calculated using the equation $Y=Y_0(e^{kt})$, where Y is the number of cells on a given day, $Y_0$ is the number of cells on day zero, t is time in days, and k is the calculated rate constant; doubling time=(0.693/k)×24 hours. (B) The clonal line R-n-1 was grown overnight in the presence (open bars) or absence (solid bars) of 1 micromolar 8-Br-cAMP and transfected with or without the indicated concentrations of H-ras plasmid. After transfections, the cells were cultured for four days with dexamethasone treatment on alternate days before plating in soft agar. Values are means ± SD of triplicate plates. (C) Several clonal lines of Rat-1 cells were transfected with various amounts of H-ras plasmids as indicated. The ability of transfected cells to form colonies in soft agar was determined. The Rat-1 lines studied were (1) R-n-1, which contains the vector pMam-neo (solid bars); (2) R-$\alpha_s$-5, which expresses exogenous wild-type $G_s\alpha$ (stipled bars); (3) R-$\alpha_s^*-1$, which expresses mutant activated $G_s\alpha^*$ (open bars); (4) R-$\alpha_s^*-2$, which expresses mutant activated $\alpha_s$ (backslashed [\] bars); and (5) R-$\alpha_s^*-7$, which expresses mutant activated $\alpha_s$ (slashed [/] bars). (D) Cells from NIH 3T3 lines n-1 and n-3 were seeded into 24-well plates ($1\times10^3$ cells per well) in 1 ml. DMEM with 10% bovine calf serum and were grown in the presence or absence of 1 micromolar 8-Br-cAMP. Solid squares represent the n-1 line cultured in the absence of 8-Br-cAMP. Open squares represent the n-1 line grown in the presence of 1 micromolar 8-Br-cAMP. Solid triangles represent the n-3 line cultured in the absence of 8-Br-cAMP. Open triangles represent the n-3 line cultured in the presence of 8-Br-cAMP. (E) n-1, $\alpha_s$-2, and $\alpha_s^*-3$ cells ($6\times10^3$ cells per well) were grown in the presence or absence of 1 micromolar dexamethasone. Solid circles represent the n-1 line cultured in the absence of dexamethasone. Open circles represent the n-1 line cultured in the presence of 1 micromolar dexamethasone. Solid squares represent the $\alpha_s$-2 line cultured in the absence of dexamethasone. Open squares represent the $\alpha_s$-2 line cultured in the presence of 1 micromolar dexamethasone. Solid triangles represent the as $\alpha_s^*-3$ line cultured in the absence of dexamethasone. Open triangles represent the $\alpha_s^*-3$ line cultured in the presence of 1 micromolar dexamethasone. (F) The clonal lines n-1 and n-3 were grown in the presence or absence of one micromolar 8-Br-cAMP. Values are means ± SD of triplicate plates. Solid bars represent n-1 cells cultured in the absence of 8-Br-cAMP. Slashed (\) bars represent n-1 cells cultured in the presence of one micromolar 8-Br-cAMP. Backslashed (\) bars represent n-3 cells cultured in the absence of 8-Br-cAMP. Open bars represent n-3 cells cultured in the presence of one micromolar 8-Br-cAMP. The experiment in each panel is representative of three experiments.

Figure 5:
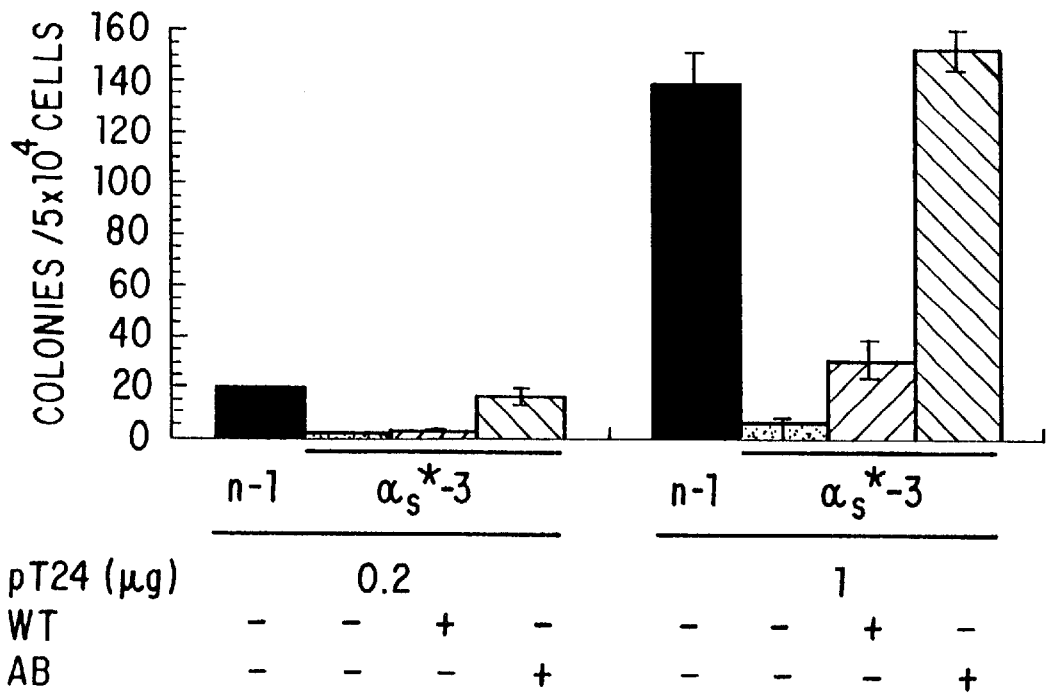

FIG. 5. Effects of the dominant negative protein kinase A ("PKA") regulatory subunit expressed from the plasmid pHL-REV$_{AB}$neo (10 micrograms; "AB") or control (wild-type PKA regulatory subunit in pHL-REV$_{WT}$neo, 10 micrograms; "WT"), on H-ras-induced transformation in NIH 3T3 clonal cell lines n-1 and $\alpha_s^*-3$. Cells were cotransfected with indicated amounts of H-ras plasmid without or with the vectors encoding the PKA regulatory subunits. After transfections, the cells were induced with dexamethasone (one micromolar) and plated onto soft agar plates to score for colony formation. Values are means ± SD of triplicate determinations. The result in each panel is representative of three experiments.

FIG. 6. Expression of adenylyl cyclase 2 (AC2) in Sf9 cells. Basal and forskolin-stimulated adenylyl cyclase activities were measured in membranes of Sf9 cells. (A) without infection (−), infected with TPO-baculovirus (TPO) or infected with AC2-baculovirus (AC2). (B) After treatment without (−) or with (+) PMA prior to preparation of membranes. (C) After treatment with the phorbol esters PDD or PMA in the presence and absence of 1 $\mu$M staurosporine (Stauro). All values are means ± SD of triplicate determinations.

FIG. 7. Effects of PMA treatment on adenylyl cyclase 2. (A) Lineweaver-Burke plot of varying ATP concentrations on AC 2 activity in control and PMA-treated cells. (B) Basal AC 2 activity in control (●) and PMA-treated(O) Sf9 cell membranes at varying $Mg^{2+}$ concentrations. Inset shows fold stimulation due to PMA treatment as a function of $Mg^{2+}$ concentration (C) Stimulation by varying concentrations of activated $G_s\alpha$ (Q227L) expressed in rabbit reticulocyte lysates of control (●) and PMA treated (O) AC2. All values are means of triplicate determinations. Coefficient of variance for B and C were less than 10%.

FIG. 8. Identification of adenylyl cyclase 2 expressed in Sf9 cells. (A) Left Panel; Commassie blue stained pattern of membranes from TPO control (−) and AC2 expressing cells. Positions of the marker molecular weights in kDa are indicated. Right Panel; immunoblot of TPO (−) and AC 2 expressing membranes with AC-Comm, an antipeptide antibody to a region common to all mammalian adenylyl cyclases. Antiserum was used at a 1:1000 dilution. Detailed immunoblotting procedures are as described in Carty et al., 1990, J. Biol. Chem. 265:6268–6273; De Vivo et al., 1992, J. Biol. Chem. 267:18263–18266). (B) Basal adenylyl cyclase activity in membranes of cells infected with TPO-baulovirus (−), AC 2-baculovirus, or F-AC2 baculovirus, the epitope tagged adenylyl cyclase 2. All values are means ± SD of triplicate determinations.

Figure 9:
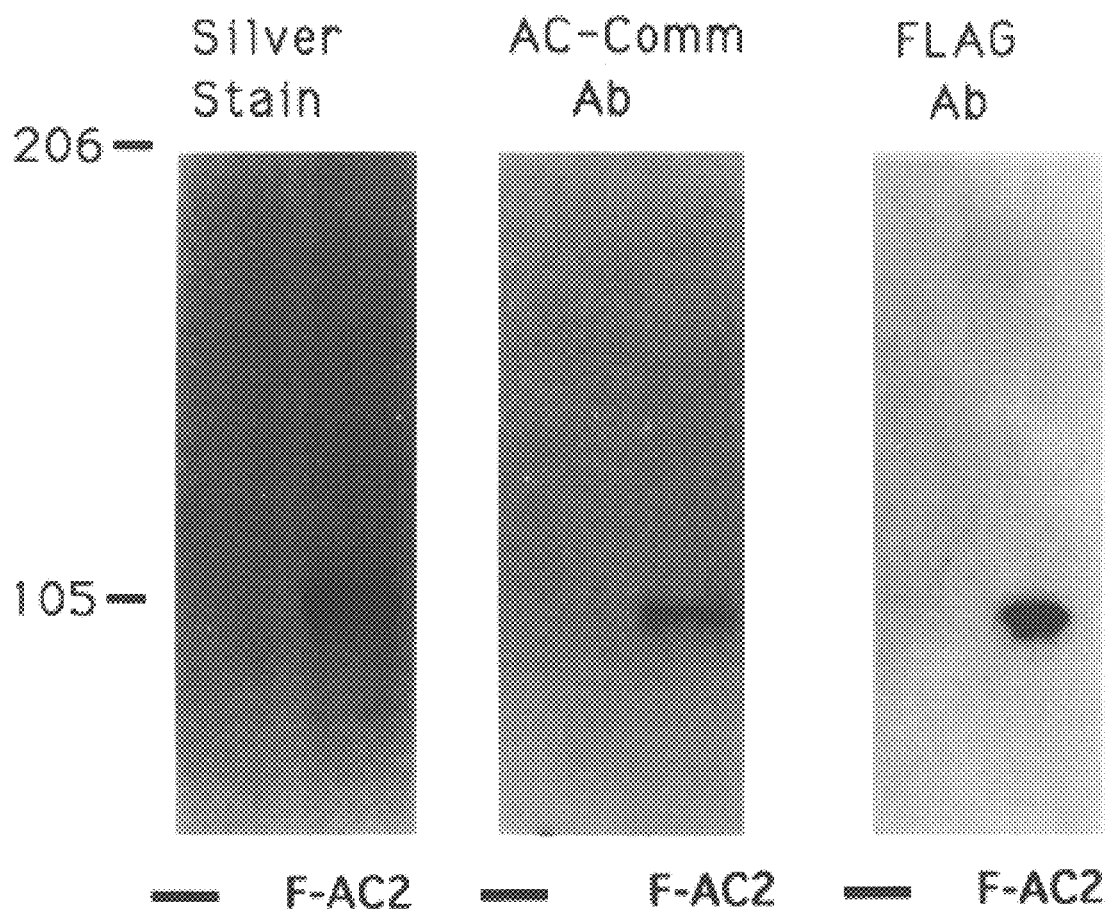

FIG. 9. Characterization of the purified epitope-tagged adenylyl cyclase 2 expressed in Sf9 cells. Membranes from TPO-baculovirus (−) and epitope tagged AC2 (F-AC2) were extracted with dodecyl maltoside and passed over the anti-FLAG affinity agarose. The agarose was washed and samples were eluted. 30 $\mu$l aliquots were resolved on SDS-polyacrylamide gels. Left panel: Silver stained profile. Middle and Right panels: Immunoblot with AC-Comm and FLAG-AB, respectively. The anti-FLAG Ab, a mouse monoclonal antibody against the epitope tagged onto AC2, was used at 30 $\mu$g/ml for immunoblotting. Marker molecular weights in kDa are shown.

FIG. 10. Activation and phosphorylation of the epitope-tagged adenylyl cyclase 2 by PMA treatment. Cells infected with TPO-baculovirus or FAC2 baculovirus were labeled with $^{32}$p (0.5 mCi/mi) for 3 hours and then treated with 1 $\mu$M PMA for 30 min. Membranes were then prepared. (A) Basal adenylyl cyclase activity in membranes from TPO or F-AC2 infected cells treated without (−) or with (+) PMA. Values are mean ± SD of triplicate determinations. (B) Membranes from cells infected with F-AC2 baculovirus and treated without (−) and with (+) 1 $\mu$M PMA were extracted and F-AC2 was purified on anti-epitope antibody affinity column. 30 $\mu$l aliquots were resolved on 6% SDS-polyacrylamide gels. Silver stained profile is shown on the left panel. An autoradiogram (9 days) of the dried gel is shown on the right panel.

FIG. 11. Amino acid (A) (SEQ ID NO:1) and nucleic acid (B) (SEQ ID NO:2) sequence of human $G_s\alpha$ (Mattera et al (1986) FEBS Lett 206: 36–40). The sequence and other information were obtained from Gen Bank. The Gen Bank accession number is X04409. The regions involved in GTPase action are indicated by lines on top of the sequences. Residues in circles are those which when mutated result in substantial inhibition of GTPase activity and an activated $G_s$-$\alpha$.

FIG. 12. Amino acid sequences of adenylyl cyclase 2 from A. rat (SEQ ID NO:3) (Feinstein et. al., 1991, Proc. Natl. Acad. Sci. USA 88:10173) and B. humans (SEQ ID NO:4) (Stengel et al, 1992, Hum Genet 90: 126). Nucleic acid sequences encoding the above rat (C.) (SEQ ID NO:5) and human (D.) (SEQ ID NO:6) amino acid sequences. The sequences and other information were obtained from Gen-Bank. Gen Bank accession numbers are M80550 and L21993 for rat and human, respectively.

Figure 13A:
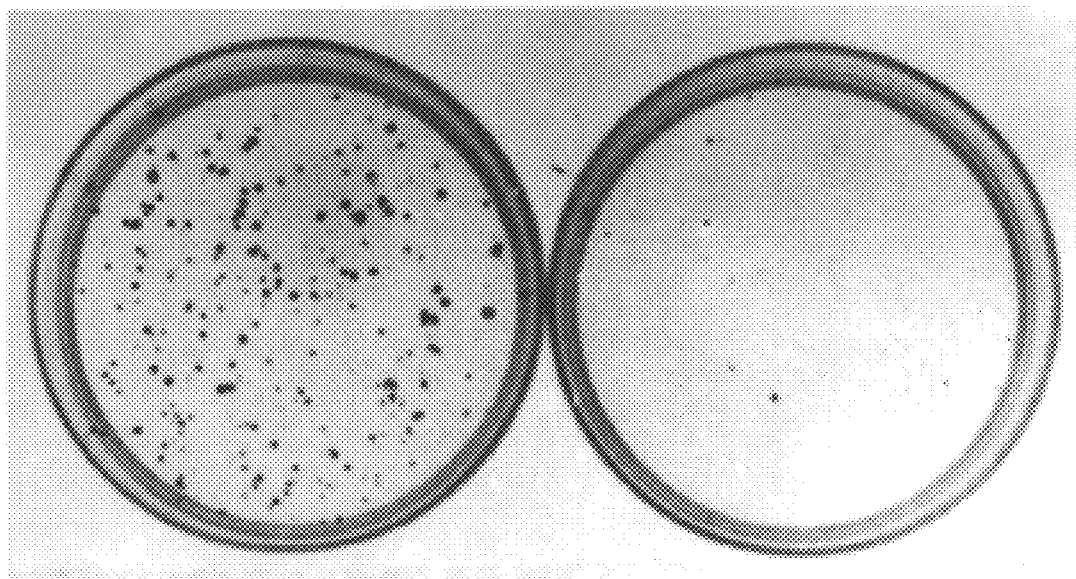
Figure 13B:
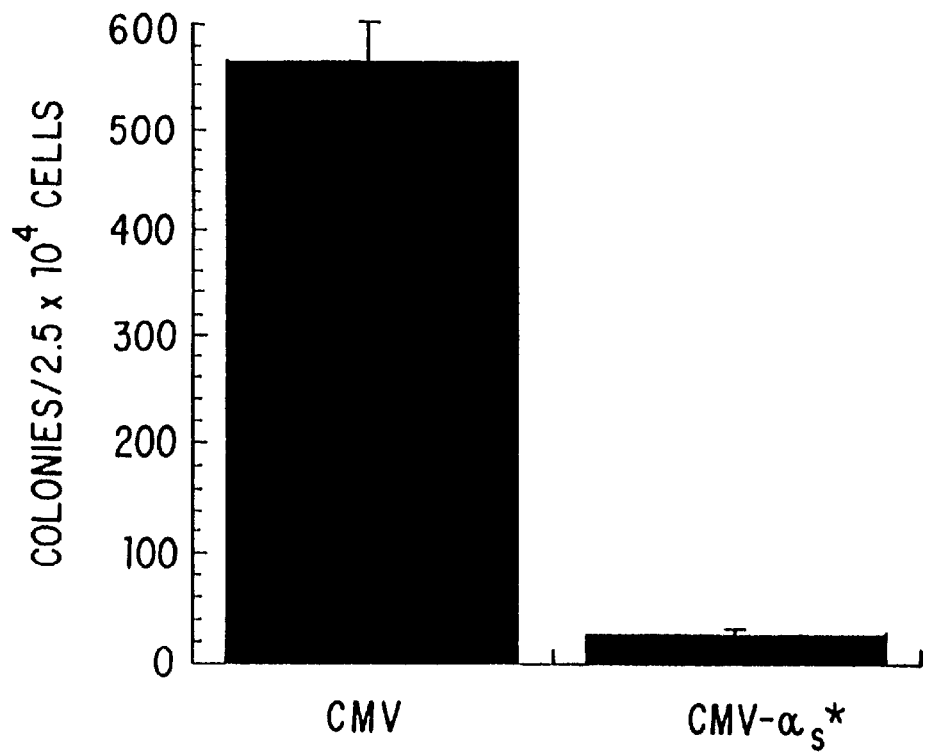
Figure 13C:
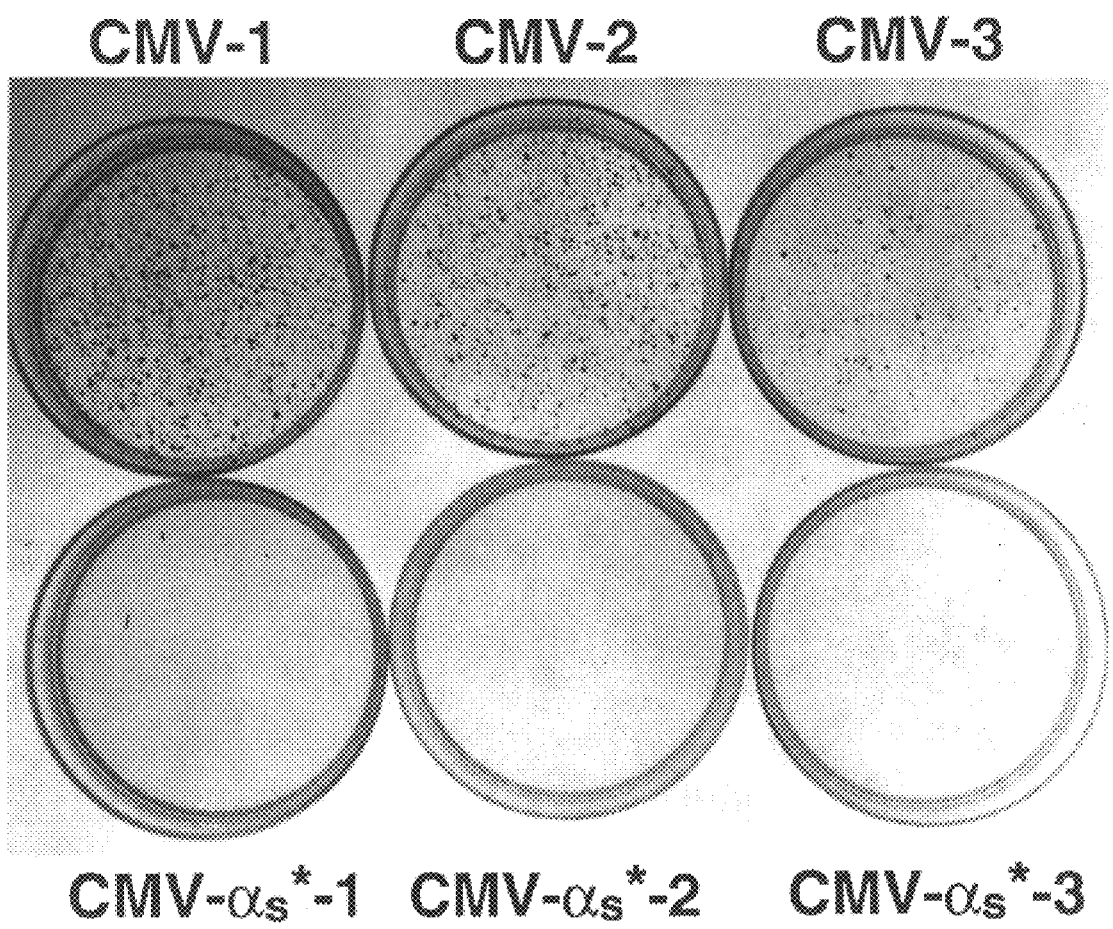

FIG. 13 Effect of $G_s\alpha^*$ on the expression of the transformed phenotype by the human breast cancer cell line MCF-7. A. Colonies in soft agar plates from control plasmid (pRC/CMV) transfected (CMV) or plasmid containing $G_s\alpha^*$ transfected (CMV-$\alpha_s^*$) MCF-7 cells. 2.5×10$^4$ cells were plated on soft agar plates in triplicate. The plates were fed every week. After three weeks the plates were stained and colonies were counted. Values are mean ± SD of triplicate determinations. Photographs of representative plates are shown above the bar graph. B. Colony formation in representative plates from three control (CMV) and three $G_s\alpha^*$ (CMV-$\alpha_s^*$) expressing plates are shown.

Figure 14B:
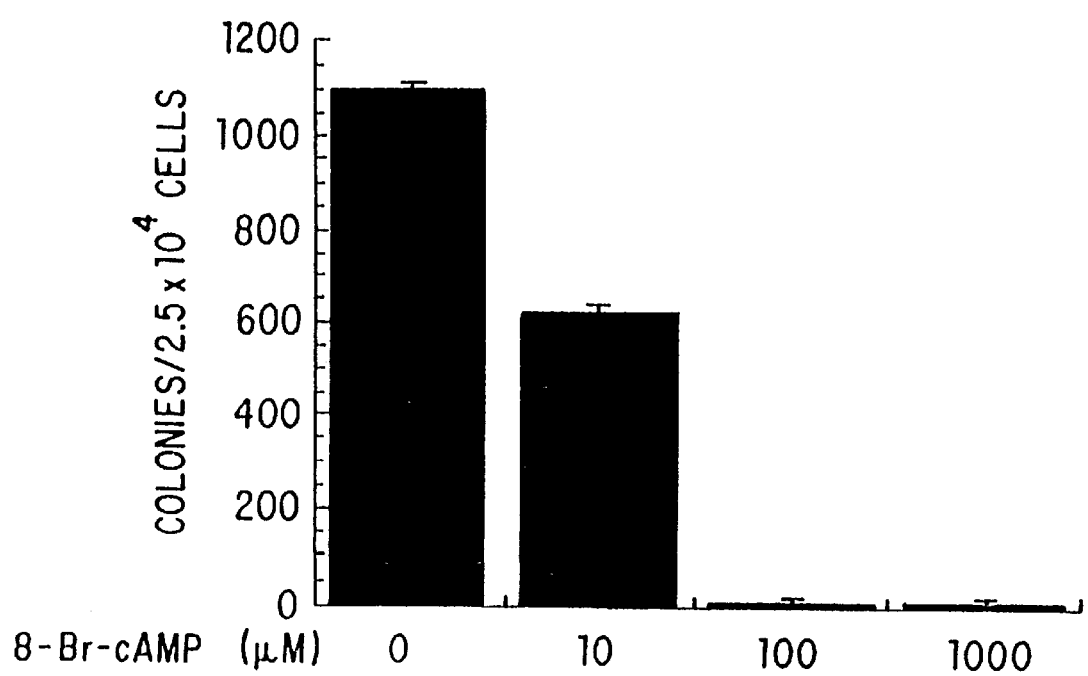
Figure 14A:
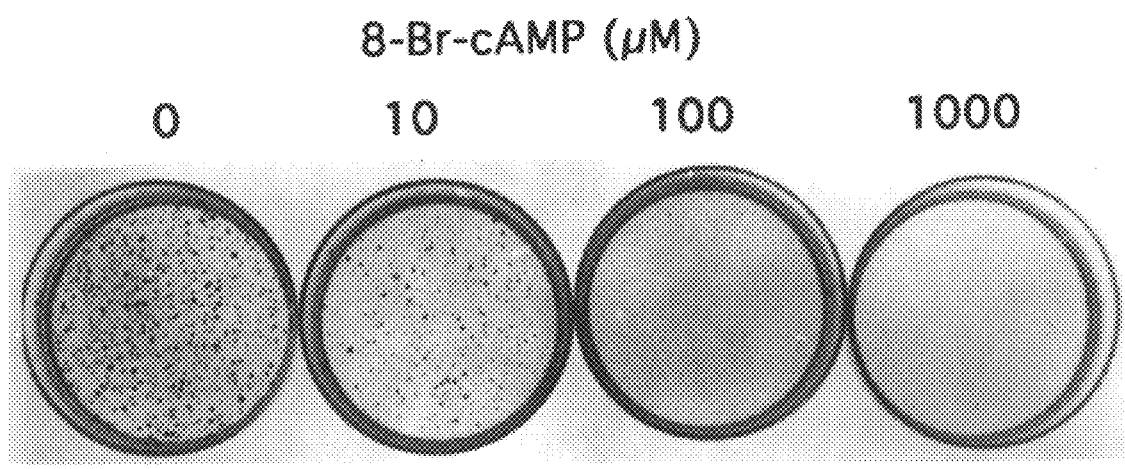

FIG. 14. Effect of exogenously added 8-Br-cAMP on the colony formation by MCF-7 cells in soft agar. 2.5×10$^4$ MCF-7 cells were plated in triplicate on soft agar plates. Indicated amounts of 8-Br-cAMP was added to the plates and the plates were maintained under culture conditions for three weeks. The plates were fed once a week. After three weeks the plates were stained and the colonies counted. Values are mean ± SD of triplicate determinations. Representative plates from the various concentrations of 8-Br-cAMP and control are shown above the bar-graph.

Figure 15:
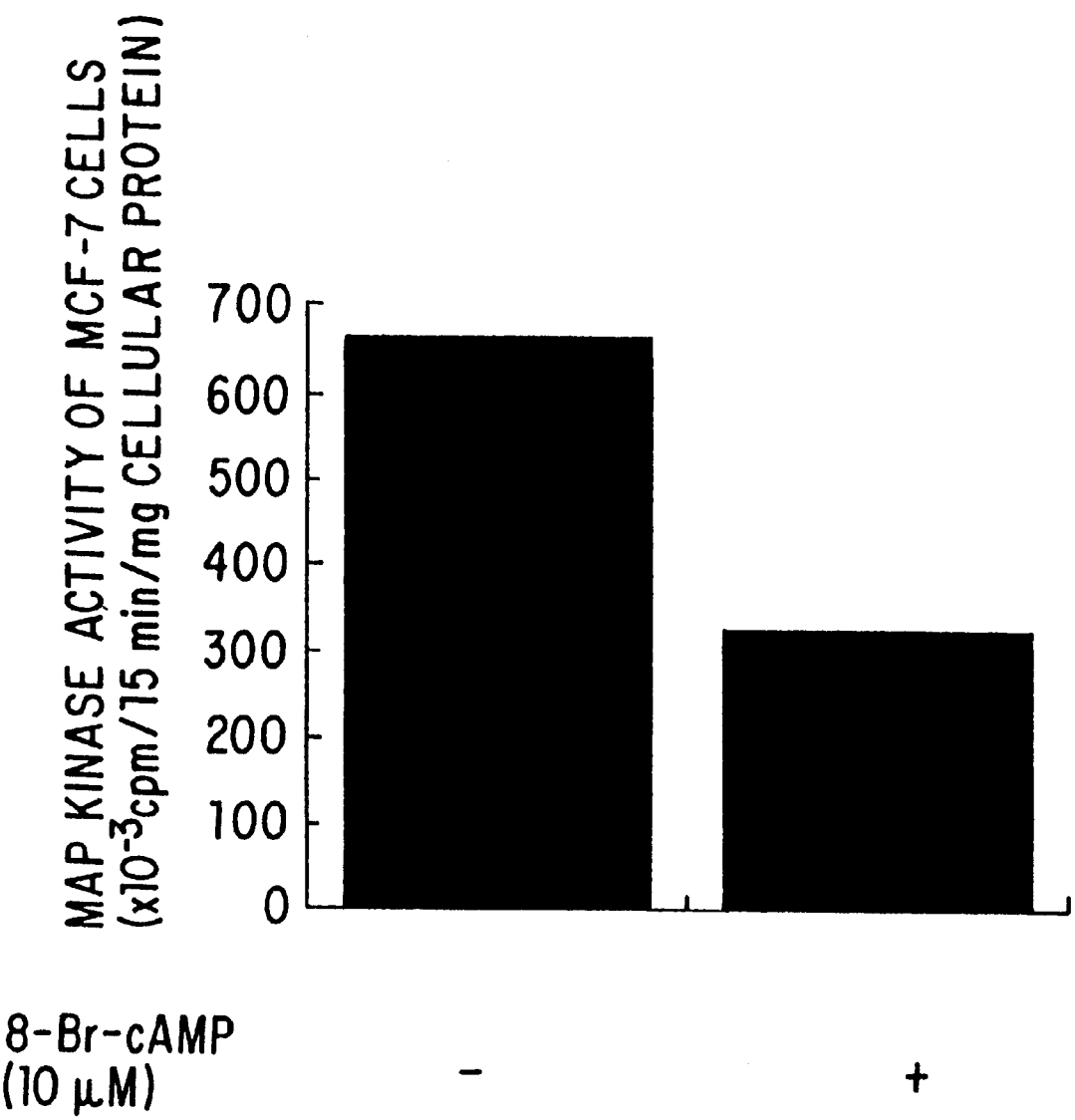

FIG. 15. Constitutive MAP-kinase activity in control and 8-Br-cAMP treated MCF-7 cells. Preconfluent MCF-7 cells were incubated for 24h in serum-free medium.The cells were further incubated for 24h in the absence and presence of 10 micromolar 8-Br-cAMP. The cells were then extracted and MAP-kinase activity was measured. The bar graph represent the sum of activities in the peak and hence no error estimates are given. Data is typical of two independent experiments.

5. DETAILED DESCRIPTION OF THE INVENTION

For clarity of presentation, and not by way of limitation, the detailed description of the invention is divided into the following subsections:

(1) $G_s\alpha^*$ in treatment of malignancy;

(2) adenylyl cyclase 2 in treatment of malignancy; and (3) further utilities of the present invention.

5.1. $G_s\alpha^*$ IN TREATMENT OF MALIGNANCY

The present invention provides for methods of treating a subject suffering from a malignancy comprising introducing $G_s\alpha^*$ into malignant cells of the subject. In related embodiments of the present invention, the development of a malignant phenotype by a non-malignant cell may be prevented, or a malignant phenotype of a malignant cell may be reduced or reversed, by the introduction of $G_s\alpha^*$ into the cell.

The subject may be a human or non-human subject. In human subjects, it may be preferable but not necessary to use human $G_s\alpha^*$ since its function is conserved in all species and since its intracellular location will prevent it from evoking an immune response.

The phrase "method of treating", as used herein, refers to methods which ameliorate a subject's clinical condition. A subject's clinical condition would be considered to be ameliorated if at least one of the following conditions are satisfied: (1) the number of malignant cells in the subject is reduced; (2) the growth rate of malignant cells or tissue is reduced; (3) the number of metastases in the subject is reduced; (4) the risk of metastases in the subject is reduced; (5) the survival of the subject is prolonged; (6) the functional abilities of the subject are improved; (7) the quality of life of the subject is improved; or (8) the risk of developing a malignancy is reduced. In preferred, non-limiting embodiments of the invention, the number or growth rate of malignant cells is reduced by at least 30% or the risk of developing a malignancy is reduced by at least 30%.

Malignancies which may be treated according to the invention involve malignant cells in which proliferation is inhibited by $G_s\alpha^*$. Such cells would not include cells which proliferate in response to elevated levels of cAMP, such as certain endocrine cells (e.g., ovary, adrenal cortex, thyroid, and some cells of the pituitary), melanocytes and osteoblasts. Similarly, cells in the crypts of Lieberkuhn in the distal ileum and colon, where the bicarbonate-chloride exchange mechanism is stimulated by cAMP resulting in loss of fluids would not be suitable recipients of $G_s\alpha^*$.

In addition, non-malignant or pre-malignant (e.g. metaplastic or dysplastic) cells may be "treated" according to the invention in order to reduce the risk that they may develop a malignant phenotype. As set forth above, cells which may abnormally proliferate or exhibit other pathophysiological characteristics in response to elevated cAMP levels may not be suitable for treatment in this manner.

According to certain specific, non-limiting embodiments of the invention, malignant mammary cells (such as human breast cancer cells) or non-malignant (or premalignant) mammary cells in which it is desirable to prevent the development of malignancy, may be the recipients of $G_s\alpha^*$. It has been determined that introduction of $G_s\alpha^*$ into the human breast cancer cell line, MCF-7, inhibits the ability of the MCF-7 cells to grow in an anchorage-independent fashion, a defining criterion for transformed cells. (see Section 8, infra)

The phrase "introduction of $G_s\alpha^*$", as used herein, refers to a means for achieving the presence of a therapeutically effective amount of biologically active $G_s\alpha^*$ protein in a cell. The term "introduction" should not be interpreted to indicate that no endogenous $G_s\alpha$ is present, but rather indicates that either no endogenous $G_s\alpha$ is present or additional $G_s\alpha$ is being provided. The phrase "therapeutically effective amount", as used herein, refers to that amount that is associated with amelioration of a subject's clinical condition (see supra). Accordingly, a therapeutically effective amount of $G_s\alpha^*$ may be achieved by a number of methods known to the skilled artisan, including, but not limited to, the introduction of either (1) DNA or RNA encoding a $G_s\alpha^*$ protein, in expressible form; or (2) $G_s\alpha^*$ protein, into a cell or, alternatively, the modification of $G_s\alpha$ already present in the cell to an activated form. These options will be discussed in greater detail below.

The term "$G_s\alpha^*$" refers to a "mutant" activated form of $G_s\alpha$ protein, which, as defined herein, exhibits reduced GTPase activity relative to the natural form of the enzyme and renders the protein in a continuously active state capable of regulating the function of its downstream effectors. In preferred embodiments of the invention, the amount of GTPase activity is reduced by at least about 50–60%. In specific, non-limiting embodiments of the invention, $G_s\alpha$ is human $G_s\alpha$, and $G_s\alpha^*$ is human $G_s\alpha$ a in which either (1) the arginine residue at position 201 is replaced by a cysteine or histidine residue; or (2) the glutamine residue at position 227 is replaced by a threonine or leucine residue.

The arginine at position 201 may be replaced by cysteine or histidine, or the glutamine residue at position 227 may be replaced by leucine, using site-directed muta-genesis techniques known to the skilled artisan. For example, and not by way of limitation, the glutamine residue at position 227 may be replaced by leucine using techniques as set forth in section 6.1.1., infra.

Nucleic acid encoding $G_s\alpha^*$, in expressible form, may be introduced into a cell using standard techniques, including, depending on the circumstances, transfection of DNA or incorporation into a suitable vector, such as a viral vector. A cDNA encoding human $G_s\alpha$ may be obtained (Mattera et al. 1986 FEBS Lett 206:36–40). The nucleic acid (SEQ ID NO:2) and amino acid (SEQ ID NO:1) sequence of human $G_s\alpha$ is set forth in FIG. 11. The regions of the protein involved in GTPase activity are underlined and amino acids that are substituted by mutations are circled.

The presence of a suitable promoter (i.e., a promotor that is efficiently expressed in the target cell type, including inducible promoters), as well as sequences required for efficient transcription and translation, provide an "expressible form" of $G_s\alpha^*$-encoding nucleic acid.

Promoters that may be useful according to the invention include the cytomegalovirus ("CMV") promoter and the Rous sarcoma virus long terminal repeat promoter.

Suitable vectors include, but are not limited to, replication deficient retrovirus, adenovirus (see, for example, Nemerow et al., 1994, Trends Cell Biol. 4: 52–55, and Kay et al., 1994, Proc. Natl. Acad. Sci. U.S.A. 91: 2353–2375; Rosenfeld et al., 1992, Cell 68: 143–155; Li et al., 1993, Human Gene Therapy 4: 403–409) and adeno-associated viruses.

For example, and not by way of limitation, a cDNA encoding $G_s\alpha^*$ which is tagged with an epitope at the N-terminus region may be cloned into a Bluescript vector containing (1) the Rous sarcoma virus long terminal repeat promoter or cytomegalovirus long terminal repeat promoter 5' to the insert and (2) the transcription termination and (3) polyadenylation signal from bovine growth hormone. This expression cassette may then be cloned into pCA13 plasmid, and cotransfected with pJM17 plasmid into HEK 293 cells (Kay et al., 1994, Proc. Natl. Acad. Sci. U.S.A. 91: 2353–2375). Recombinant adenovirus which expresses $G_s\alpha^*$ may be identified using oligonucleotide probes encoding $G_s\alpha^*$ (Graham and Prevec, 1991, in "Methods in Molecular Biology: Gene Transfer and Expression Protocols", vol. 7, E.J. Murray, ed. (Humana Press Inc., Clifton, N.J.). The functional capability of the recombinant virus may be tested by its capability to raise intracellular cAMP levels in the cycmutant of the mouse S49 lymphoma cell line. This mutant S49 cell line lacks $G_s$-$\alpha$ message or protein (Harris B. A. et. al.; 1985, Science 229:1274–1277) and hence may be used as a suitable assay system for the virus. The recombinant virus may then be allowed to infect cells of a target tissue, for example, by direct injection into a tumor mass.

In specific, non-limiting embodiments of the invention, where the target cells for introduction of $G_s\alpha^*$ are mammary cells, malignant or non-malignant, methods for introducing viral vectors into mammary gland tissue, as set forth in Gould, et al., U.S. Pat. No. 5,215,904, issued Jun. 1, 1993, and/or Archer et al., 1994, Proc. Natl. Acad. Sci. U.S.A. 91:6840–6844, may be utilized. Arteries involved in blood supply to the breast may be used to introduce the virus containing $G_s\alpha^*$. Possible sites of entry could include the medial mammary arteries and the lateral mammary branches of the lateral thoracic artery.

In additional embodiments, therapeutically effective amounts of $G_s\alpha^*$ protein may be introduced into cells. For example, $G_s\alpha^*$ may be "piggy-backed" into a cell in conjunction with another protein for which the target cell has a receptor.

In certain embodiments of the present invention, it may be desirable to introduce $G_s\alpha^*$ into cells ex vivo. For example, it may be desirable to treat bone marrow collected from a patient for the purposes of autologous transplant so as to eliminate or decrease malignant cells or malignant characteristics of cells. To this end, transfection techniques, viral vectors, and other methods as set forth above may be applied to cells in culture.

5.2. ADENYLYL CYCLASE 2 IN TREATMENT OF MALIGNANCY

The present invention provides for methods of treating a subject suffering from a malignancy comprising introducing adenylyl cyclase 2 (AC 2) into malignant cells of the subject such that a therapeutically effective amount of AC 2 is present in the cell. In related embodiments of the present invention, the development of a malignant phenotype by a cell may be prevented, or a malignant phenotype of a cell may be reduced or reversed, by the introduction of AC 2 into the cell. Definitions of "subject", "methods of treatment", "introduction", "therapeutically effective amount" etc., are as set forth above.

Cells and tissues, malignant or premalignant or potentially malignant, which may benefit from the introduction of AC 2 may include cells and tissues which constitutively express AC 2, but in which an increase in AC 2 may be beneficial. The term "Potentially malignant cells", as used herein, refers to cells which have an increased probability of becoming malignant relative to normal cells. For example, AC 2 is constitutively expressed in brain and lung and airway smooth muscle. The introduction of AC 2 into malignant brain cells or lung tissue may be beneficial if intracellular cAMP levels are elevated by tyrosine kinase pathways and if one of the contributing factors in the development of malignancies is activation of the tyrosine kinase pathways. In these situations proliferative signaling from the tyrosine kinase pathway may be reduced or prevented by the concomitant elevation of cAMP levels.

Cells and tissues, malignant, premalignant, or potentially malignant, which do not constitutively express AC 2 may also benefit from its introduction. For example, cells which exhibit activated phospholipases C or D and protein kinase C (enzymes which are frequently found elevated in malignant cells) but which lack AC 2 may benefit from the introduction of AC 2, because, as demonstrated in Section 7, below, protein kinase C modifies and stimulates AC 2. This may increase cellular cAMP levels, which, depending on the cell type, may inhibit cellular proliferation as well as the malignant phenotype.

In order to determine whether an increase in AC 2 may be beneficial, a sample of cells (e.g., tumor cells) from a subject may be transfected with AC 2, and the proliferation and phenotype of transfected cells evaluated. If the proliferative capacity and/or transformed phenotype is diminished by transfection of AC 2, then the introduction of AC 2 into that cell type may be considered sufficiently likely to be beneficial.

In a preferred embodiment of the invention, AC 2 may be introduced into breast cancer cells. It has been determined that increased levels of cAMP inhibit the constitutively elevated MAP-kinase activity, suppress the expression of transformed phenotype as assessed by anchorage independent growth in soft agar and inhibit epidermal growth factor-stimulated DNA synthesis in the human breast cancer cell line, MCF-7 (See Section 8, and especially FIGS. 14 and 15).

The full length rat cDNA for AC2 has been cloned and sequenced (FIG. 12C; SEQ ID NO:5). A partial human clone that encodes about 50% of AC 2 is also available (FIG. 12D; SEQ ID NO:6). Since the sequences of the same isoforms of mammalian adenylyl cyclases from different species are very highly (<90%) conserved (Premont, 1994, Meth. Enzmol. 238:116–127) the full length human clone may be obtained using standard laboratory techniques to identify a cDNA clone encoding full-length human Ac 2. Expression constructs and vectors may be used, as described for $G_s\alpha$ in the preceding section. Similarly, methods for introducing AC 2 protein, as set forth regarding $G_s\alpha^*$ in the preceding section, may be utilized.

5.4. FURTHER UTILITIES OF THE INVENTION

The present invention may, in addition to the above uses, be used to reduce or prevent cell proliferation, where such proliferation may be undesirable. Accordingly, the present invention provides, in non-limiting embodiments, for methods of reducing or preventing the proliferation of cells in a subject comprising introducing a gene encoding mutant activated $G_s\alpha$ or adenlyl cyclase 2, into the cells, such that a therapeutically effective amount of mutant activated $G_s\alpha$ or AC 2 protein is produced in the cells. Alternately, protein may be introduced directly. In this context "therapeutically effective amount" indicates that proliferation has been reduced by at least about 30%. In particular, non-limiting embodiments, the present invention may be utilized in the prevention of restenosis following coronary artery angioplasty, and in the treatment of asthma.

It has been demonstrated that elevation of intracellular cAMP levels inhibits proliferation of aortic smooth muscle cells (Assender J. W. et al., 1992, Biochem J. 288:527–532). It has also been shown that protein kinase A antagonizes PDGF-induced MAP-kinase (Graves et al., 1993, Proc. Natl. Acad. Sci. USA 90:10300–10304) activated proliferation of human arterial smooth muscle cells. Thrombin and PDGF which are known activators of the MAP-kinase pathway stimulate proliferation of the human vascular smooth muscles (Kanthou et al., 1992, FEBS Lett 314: 143–48). Because proliferation of smooth muscle cells is believed to play a role in restenosis of coronary arteries following angioplasty (Baringa, 1994, Science 265:738), the use of $G_s\alpha^*$ to increase intracellular cAMP concentrations in these cells, thereby stimulating protein kinase A activity, may be used to prevent restenosis. Accordingly, $G_s\alpha^*$ may be introduced into coronary artery smooth muscle cells using techniques as set forth in Section 5.1., above. In a specific, non-limiting embodiment of the invention, an adenovirus vector, as described, may be used to introduce nucleic acid encoding a $G_s\alpha^*$. The coronary artery smooth muscle cells may be exposed to effective amounts of such a viral vector at the time of angioplasty. The coronary arteries may be exposed by sterile surgical procedure and a double barrel angioplasty catheter may be used to introduce the virus. Inflation of both balloons allows for the selective introduction of the recombinant virus in the central space of the catheter. Such a technique has been recently used to selectively and successfully introduce the exogenous thymidine kinase gene into porcine arteries (Ohno et al., 1994, Science 265: 781–784). The local expression of $G_s\alpha^*$ may be useful in suppression of proliferation that often accompany the injury to the blood vessel upon balloon angioplasty. Since proliferation of arterial smooth muscle is stimulated by platelet derived growth factor acting through receptor tyrosine kinase, introduction of AC 2 may also be useful in the suppression of proliferation.

In further embodiments, the methods of the invention may be useful in the treatment of asthma and chronic obstructive pulmonary disease resulting from bronchoconstriction. Increased cAMP levels result in bronchodilation and β-adrenergic agonists that raise AMP levels have become among the most popular therapies for bronchodilation (Rall, 1990, in Pharmacological Basis of Therapeutics , 8th Edition, Pergamon Press, pp. 632–635). Introduction of $G_s\alpha^*$ or AC 2 may result in constitutive elevation of cAMP and thus provide relief for several weeks especially in patients where the nasal sprays that use β-adrenergic receptor agonists are not effective due to down regulation of β-adrenergic receptors. Actuated $G_s\alpha$ or AC 2 may be introduced by recombinant viruses, as described above, which may be introduced into the respiratory track by perfusion. Alternatively, activated $G_s\alpha$ may be introduced by the use of cationic liposomes (Alton, E. and Gelddes, D., 1994, Nature Gen. 8:8-9).

6. EXAMPLE: SUPPRESSION OF RAS-INDUCED TRANSFORMATION OF NIH 3T3 CELLS BY ACTIVATED $G_s\alpha$

6.1. MATERIALS AND METHODS

6.1.1. PREPARATION OF CELL LINES

Q227L $G_s\alpha$ was prepared by site-directed mutagenesis by polymerase chain reaction (PCR). Briefly, oligonucleotides containing the mutated sequence (638 A->T and 639 G->T) were used to generate a PCR fragment that encodes a Leu residue at position 227 instead of the native Gln. The wild-type $G_s\alpha$ gene was digested with Bam HI and the corresponding wild-type fragment was replaced with the PCR fragment encoding the mutant sequence. The presence and position of the mutation were verified by DNA sequencing. The wild-type $G_s\alpha$ and mutant $G_s\alpha$ were then transferred into the mammalian expression vector pMam-neo (DeVivo et al., 1992, J. Biol. Chem. 267: 18263). Individual clonal lines transfected with either vector alone, vector containing wild-type $G_s\alpha$, or vector containing Q227L $G_s\alpha$, were isolated by G-418 selection after calcium phosphate transfection (Id.).

6.1.2. MEASUREMENT OF DNA SYNTHESIS

Cells ($10^4$ per well) were plated in 24-well plates in 1 ml. of Dulbecco's modified Eagles medium (DMEM) containing 10% calf serum, and were induced with 1 micromolar dexamethasone for two days. On the third day, the medium was replaced with 1 ml. of fresh medium containing 1% calf serum. On the fourth day, 1 microcurie of [$^3$H]thymidine was added along with dexamethasone and the cells were cultured for 24 hours. The cells were then washed twice with phosphate-buffered saline. The amount of radioactivity precipitated by 5% trichloroacetic acid after incubation of the cells was estimated by liquid scintillation counting.

6.1.3. MEASUREMENT OF MAP KINASE ACTIVITY

Cells were extracted and the extract was resolved on Mono-Q columns of a fast protein liquid chromatography (FPLC) system. MAP kinase activity in the FPLC fractions was measured with a synthetic peptide containing amino acids 662 to 681 of the epidermal growth factor as receptor (Gupta et al., 1992, J. Biol. Chem. 267: 7987).

6.1.4. MEASUREMENT OF cAMP

Clonal cells were treated with 1 micromolar dexamethasone on alternate days for one week. The cells were then labelled with [$^3$H]adenine (2 microCuries/ml.) for 24 hours. Accumulation of cAMP was measured for 30 minutes in the presence of 1-methyl-3-isobutylxanthine (1 mM). Cells were extracted in 5% trichloroacetic acid, 1 mM adenosine triphosphate (ATP), and 1 mM cAMP. [$^3$H]cAMP and [$^3$H]ATP were separated by sequential chromatography on Dowex-50 and neutral alumina.

6.1.5. TRANSFORMATION ASSAYS

After transfection wit h the H-ras plasmid, pT24, which contains an activated c-H-ras oncogene isolated from human T24 bladder carcinoma cells (Goldfarb et al., 1982, Nature 296: 404), cells were induced for either one day (NIH 3T3 cells) or three days (RAT-1 cells) with 1 mM dexamethasone before plating on soft agar plates. Procedures for the colony formation assay were as described in DeVivo et al., 1992, J. Biol. Chem. 267: 18263. Transfection efficiencies for the various NIH 3T3 clonal lines were very similar (Chen J.(1994) PH. D. Thesis CUNY NY). No differences were found in the transfection efficiencies for the different RAT-1 clonal lines.

6.1.6. IMMUNOPRECIPITATION

[$^{35}$S]methionine-labelled H-Ras was immunoprecipitated from extracts of NIH 3T3 cell lines n–1 and $\alpha_s$-3, which were cotransfected with 20 micrograms of genomic NIH 3T3 DNA and 1 microgram of pRSV 1.1 DNA (a cDNA which confers hygromycin resistance), with or without 5 micrograms of H-ras plasmid. After transfection, cells were induced with 1 micromolar dexamethasone for 1 day and cultured in medium containing 400 micrograms/ml hygromycin B. The medium was changed every 3 days. After 1 week, cells were treated with one micromolar dexamethasone again. One week later, $3 \times 10^6$ cells were labelled with 0.25 mCi of [$^{35}$S]methionine for three hours. Cells were then lysed, and Ras was immunoprecipitated with Y13-259 anti-Ras monoclonal antibody, according to a protocol provided by oncogene Science, Inc.. The immunoprecipitated products were resolved on SDS-polyacrylamide gels (15%) and visualized by autoradiography.

6.2. RESULTS $G_s\alpha$, in which Gln 227 was mutated to Leu (Q227L), was prepared by site-directed mutagenesis. NIH 3T3 cells were transfected with either wild-type $G_s\alpha$, mutant Q227L $G_s\alpha$ ($\alpha_s$*) in the vector pMam-Neo(pMN), or vector alone. Selected cells were individually plated, and several clonal lines were established (DeVivo et al., 1992, J. Biol. Chem. 267:18263). Expression of the insert was induced by addition of dexamethasone and monitored by measurement of cAMP. Two NIH 3T3 clones having a 60–100% increase in basal cellular concentrations of cAMP were used for further studies.

The effects of expression of $\alpha_s$* on H-Ras-stimulated mitogenesis and on mitogen-activated protein (MAP) kinase activity were determined.

Expression of $\alpha_s$* alone did not appear to alter the rate of DNA synthesis, as measured by [$^3$H]thymidine incorporation. Cells transfected with pT24, an H-ras-containing plasmid, showed a five-fold increase in the rate of DNA synthesis. However, concurrent expression of $\alpha_s$* was found to suppress the H-Ras-induced increase in DNA synthesis (FIG. 2A).

The mitogenic signal from Ras is transmitted through the MAP kinase pathway (Marx, 1993, Science 260: 1588; Davis, 1993, J. Biol. Chem. 268: 14553; Blenis, 1993, Proc. Natl. Acad. Sci. U.S.A. 90: 5889). The effect of expression of $\alpha_s$* on H-Ras-induced MAP kinase activity was therefore determined. Expression of $\alpha_s$* suppressed H-Ras-stimulated MAP kinase activity by about 50%, similar to its effect on DNA synthesis (FIG. 2B).

In order to establish that the observed reduction of H-Ras-stimulated MAP kinase activity by $\alpha_s$* was not due to clonal variation, another clonal line expressing $\alpha_s$* was studied. Both clonal lines expressing $\alpha_s$* showed increased intracellular concentrations of cAMP as compared to control vector-transfected lines. After transfection with H-ras containing pT24, both $\alpha_s$*-expressing lines showed a 50% reduction in H-Ras-stimulated MAP kinase activity as compared to that of the control cell lines (see Table 1).

TABLE 1

| Cell lines | cAMP* | MAP kinase Activity** |
|---|---|---|
| n – 1 | 0.95 ± 0.005 | 4.80 |
| $\alpha_s$* – 3 | 1.58 ± 0.16 | 2.84 |
| $\alpha_s$* – 14 | 2.02 ± 0.21 | 2.47 |

Figure 3C:
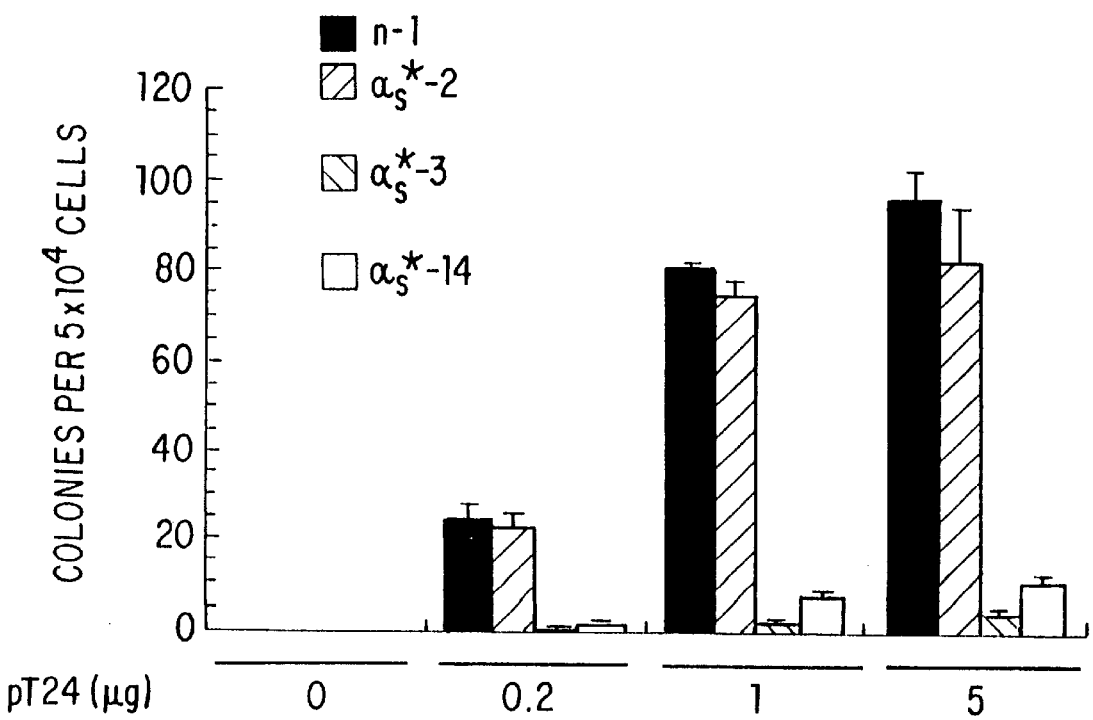
Figure 3A:
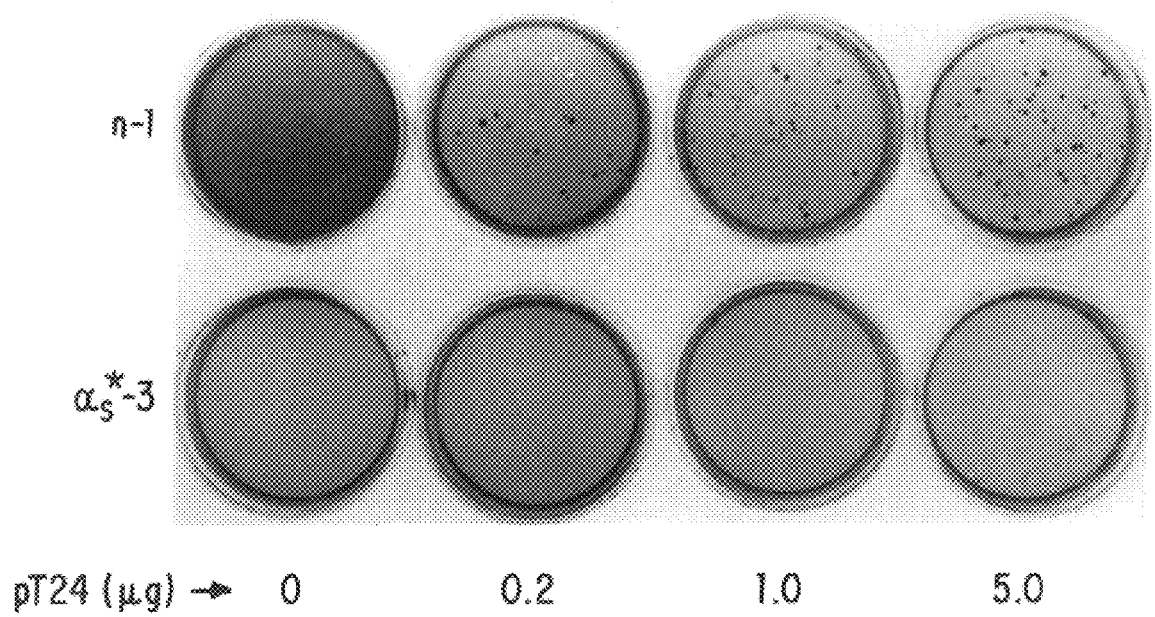

*calculated as [$^3$H]cAMP/([$^3$H]cAMP + [$^3$H]ATP) × $10^3$
**CPM/15 min./1 microgram cellular protein × $10^{-3}$ Because H-ras-induced mitogenesis leads to transformation of NIH-3T3 cells, the affects of $\alpha_s$* expression on Ras-induced transformation of these cells was tested. Expression of $\alpha_s$* resulted in an almost total blockade of H-Ras-induced transformation at all concentrations of H-Ras plasmid tested (FIG. 3A). Transfection efficiencies for the various clonal lines were very similar.

Figure 3B:
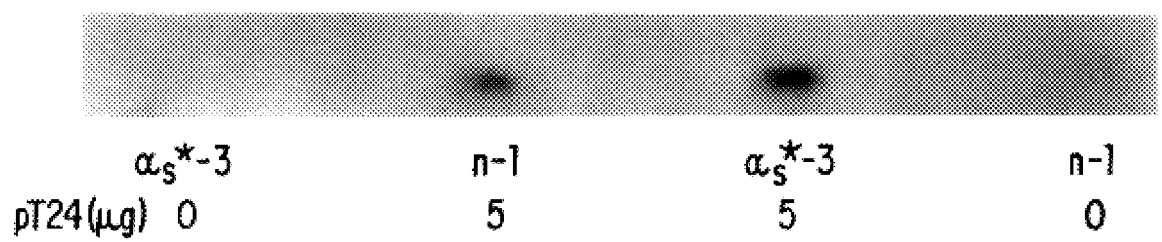

To determine if the transfected H-ras was expressed in similar amounts in both control and $\alpha_s$*-expressing cells, proteins were labelled with [$^{35}$S]methionine and H-Ras was immunoprecipitated with Y13-259, a monoclonal antibody to Ras. Upon transfection with H-ras plasmid, there was an increase in the amount of immunoprecipitated H-Ras protein, and expression of $\alpha_s$* did not affect this increase (FIG. 3B). Therefore, the observed suppression of transformation did not result from suppression of synthesis of H-Ras protein.

H-Ras-induced transformation of two separate clonal lines expressing $\alpha_s$* were also compared to a clonal line expressing wild-type $G_s\alpha$ and a control clone transfected with vector only. Expression of exogenous wild-type $G_s\alpha$ did not increase cellular cAMP concentrations and did not suppress transformation at any of the concentrations of H-ras plasmid tested, but in both clonal lines expression of $\alpha_s$* blocked H-ras-induced transformation at all concentrations of H-ras plasmid tested (FIG. 3C).

Figure 4A:
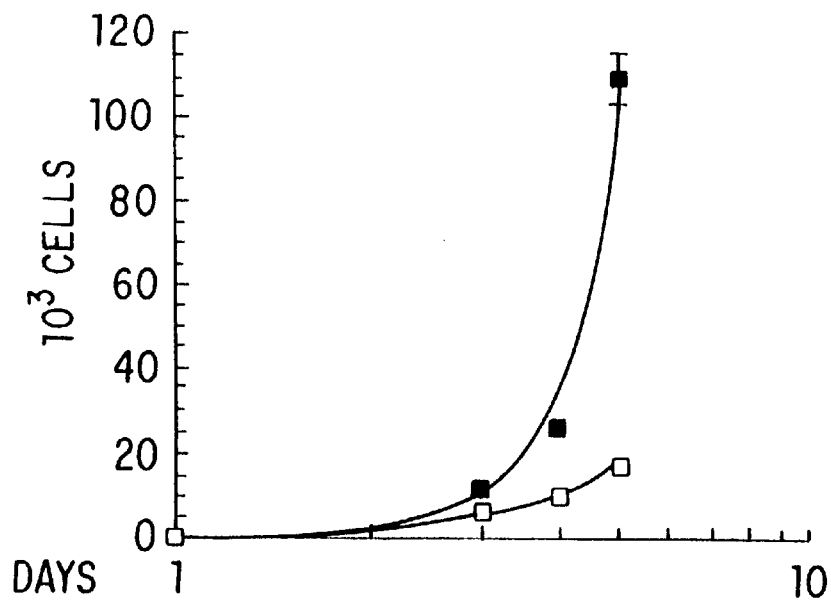
Figure 4B:
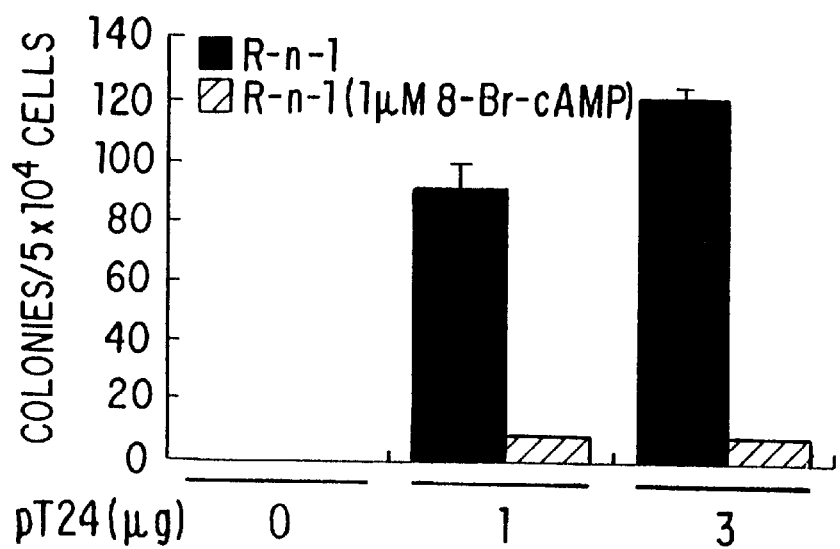
Figure 4C:
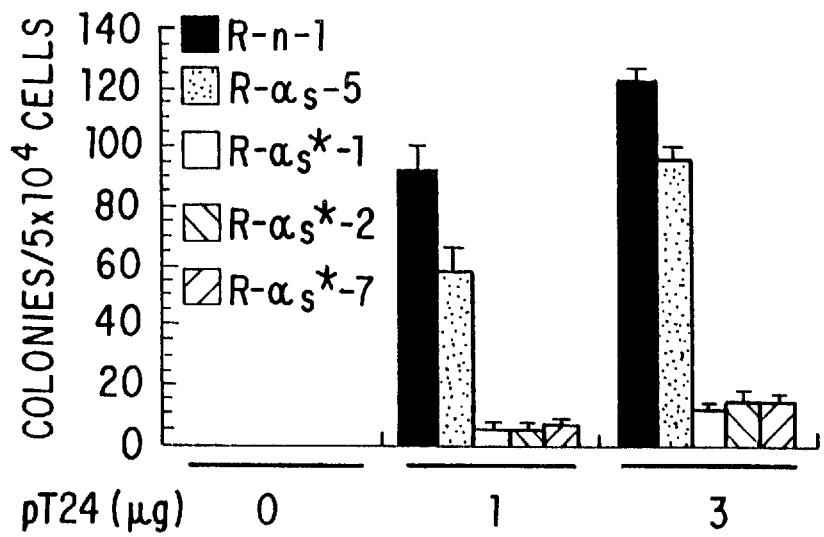

Decreasing the cellular concentrations of cAMP promotes cell division in RAT-1 cells (van Corven et al., 1989, Cell 59: 45), but no such effects have been described for NIH 3T3 cells. Accordingly, it was determined whether an increase in the cellular concentration of cAMP or the expression of $\alpha_s$* would suppress mitogenesis in RAT-1 or NIH 3T3 cells. It was found that addition of 8-Br-cAMP suppressed the proliferation of Rat-1 cells (FIG. 4A) and suppressed H-Ras-induced transformation (FIG. 4B). Further, expression of $\alpha_s$* was observed to suppress H-Ras-induced transformation of the Rat-1 lines (FIG. 4C).

Figure 4D:
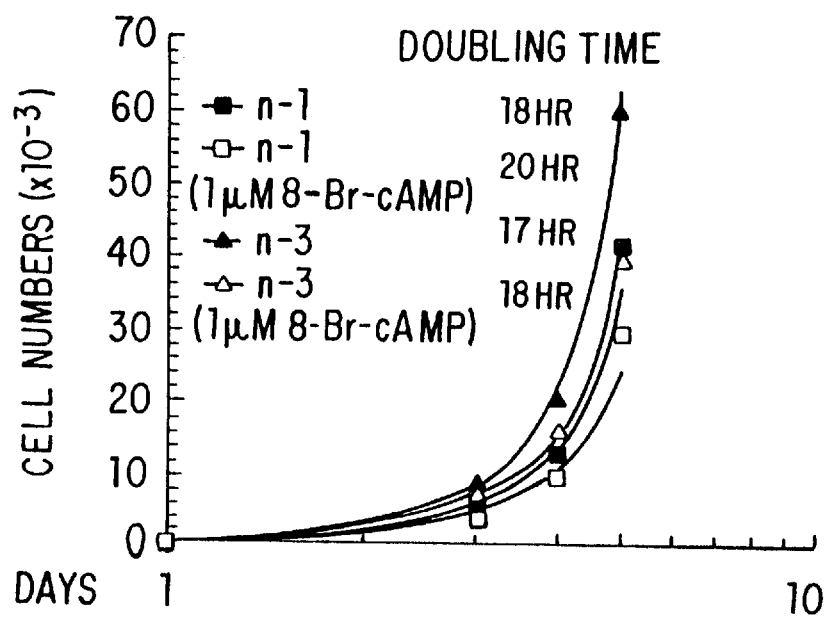
Figure 4E:
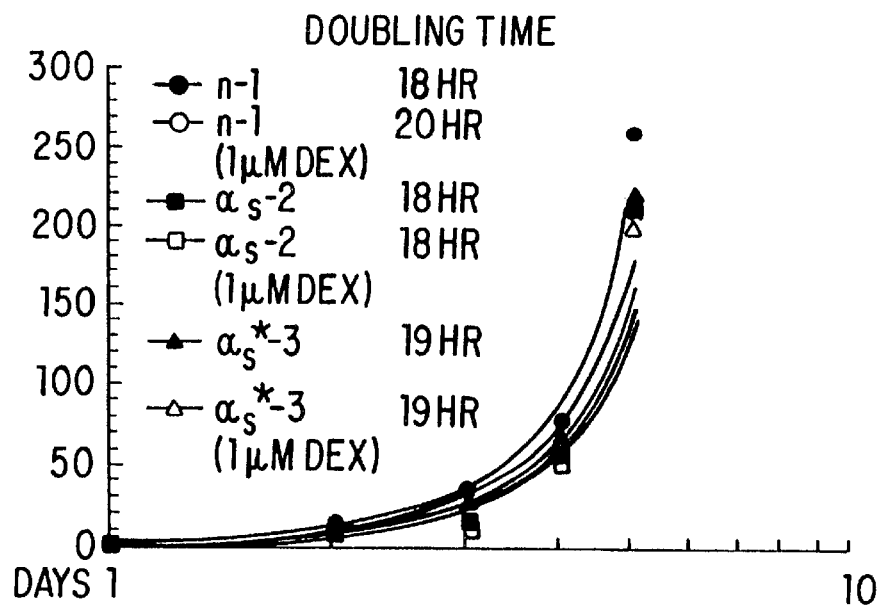
Figure 4F:
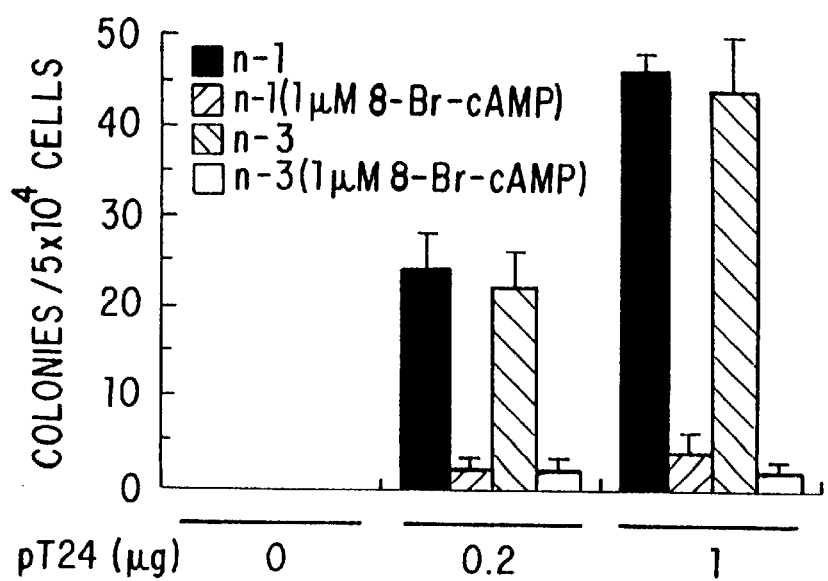

In contrast, addition of 8-Br-cAMP or expression of $\alpha_s$* was found not to affect the proliferation of NIH 3T3 cells (FIG. 4D). However, in two control clonal lines, incubation with 8-Br-cAMP resulted in suppression of H-Ras-induced transformation (FIG. 4E).

To ascertain whether $\alpha_s$* suppressed H-Ras-induced transformation by causing synthesis of cAMP and activation of protein kinase A ("PKA"), the effect of a dominant negative PKA subunit on the effect of $\alpha_s$* was studied. The dominant negative regulatory subunit blocks activation of PKA in NIH 3T3 cells (Clegg et al., 1987, J. Biol. Chem. 262: 13111). The dominant negative PKA regulatory subunit or wild-type PKA regulatory subunit was transfected, along with two concentrations of H-ras plasmid, into control and $\alpha_s$*-expressing cells. Expression of dominant negative but not wild-type PKA completely blocked the suppressive effect of $\alpha_s$* expression on H-Ras-induced transformation (FIG. 5). These results indicate that the effects of $\alpha_s$* are mediated through cAMP and PKA.

Ras signalling through the MAP kinase pathway is crucial for proliferative responses (Marx, 1993, Science 260: 1588; Davis, 1993, J. Biol. Chem. 268: 14553; Blenis, 1993, Proc. Natl. Acad. Sci. U.S.A. 90: 5889). Both the duration (Traverse et al., 1992, Biochem. J. 288:351) and amplitude of MAP kinase activity may be important factors when MAP kinase activity gets converted into a biological response. In some situations, partial inhibition of MAP kinase activity appears to translate into an almost total loss of biological response (FIG. 2) (Cook et al., 1993, EMBO J. 12: 3475). It is possible that negative biochemical integration between the signalling pathways may be achieved by lowering the positive signal below the threshold that triggers the biological response. Alternatively, $\alpha_s$* may inhibit transformation by inhibiting other signalling pathways.

Alteration in cellular concentration of cAMP by itself does not affect regulation of mitogenesis in NIH 3T3 cells or in most other mammalian cell types (Spada et al., 1992, Trends Endocrinol. Metab. 10: 355). Mutations in ras occur commonly in human tumors (Barbacid, 1987, Ann. Rev. Biochem. 56:779). Thus, activated $G_s\alpha$ may suppress transformation of other cell types.

Because expression of $\alpha_s$* only modestly increases the cellular concentrations of cAMP, it is possible that the blockade of transformation by $\alpha_s$* can be achieved without raising cellular cAMP concentrations to deleterious levels. NIH 3T3 cells are on the verge of transformation (Rigby, 1982, Nature 297: 451) and can be transformed without the introduction of foreign oncogenes (Rubin and Xu, 1989, Proc. Natl. Acad. Sci. U.S.A. 87:1860). The use of such a system heightens the potential significance of the foregoing observations by indicating that $\alpha_s$* can block the transformation of cells that have already substantially progressed through the multiple steps involved in neoplastic transformation. Therefore, targeted implantation of $\alpha_s$* may be a useful strategy for preventing the development of cancer in some predisposed cells or tissues.

7. EXAMPLE: PHORBOL ESTER-INDUCED STIMULATION AND PHOSPHORYLATION OF ADENYLYL CYCLASE 2

AC 2 was expressed in Sf9 cells by baculovirus infection. In this system, it was demonstrated that AC 2 is phosphorylated and stimulated by activation of protein kinase C, establishing that, in addition to G protein subunit regulation, covalent modification of an effector is a distinct mechanism by which signals may be transmitted through G protein pathways.

7.1. MATERIALS AND METHODS

7.1.1. MATERIALS

AC-comm rabbit antiserum was raised against the peptide sequence IGARKPQYDIWGNT (SEQ ID NO:7), common to the C-terminal region of all cloned mammalian adenylyl cyclases. When tested against the recombinant AC 2 and AC 6 expressed in Sf9 cell membranes, the antibody recognized proteins of appropriate sizes in immunoblots. Adsorption of the anti-body with the appropriate peptide vitiated recognition of adenylyl cyclase. Recombinant Q227L $G_s\alpha$ used in these experiments was a gift of Drs Juan Codina and Lutz Birnbaumer and was synthesized with the TnT in vitro translation system (Promega). Sf9 cells and pVL-1392 were obtained by the Mount Sinai Protein Expression Core Facility from Dr. Max Summers. Baculogold virus was purchased from Pharmingen. Sf9 serum-free cell medium was from Gibco BRL or Sigma. Dodecyl-maltoside and 2-[N-morpholino] ethane sulfonic acid (MES) were from Sigma. Anti-FLAG M2 affinity gel and Anti-FLAG antibody were from Kodak-IBI. [$a^{32}$P]ATP (25 Ci/mmol), and [$^{32}$P]H$_3$PO$_4$ were from ICN. Sources of all other materials were described in Jacobowitz et al., 1993, J. Biol. Chem. 268:3829–3832; Carty et al., 1990, J. Biol. Chem. 265:6268–6273; Premont and Iyengar, 1988, J. Biol. Chem. 263:16087–16095; and De Vivo et al., 1992, J. Biol. Chem 267:18263–18266.

7.1.2. CONSTRUCTION OF AC2 AND FLAG AC2 RECOMBINANT BACULOVIRUS

AC2 cDNA was excised from pBSII-AC2 and inserted into pVL-1392. Recombinant plasmids were screened for proper orientation by restriction digests. pVL-1392-AC2 was then used to construct pVL1392-F-AC2. The FLAG epitope DYKDDDDK was incorporated into pVL-1392-AC2 by PCR mutagenesis. The 5' primer, 0J049 (TACAAGCGGCCGCATGGACTACAAGGACGACGA-CGATAAGCGGCGGCGCCGCTACC) (SEQ ID NO:8), contained a NotI restriction site followed by codons for an initiator Met, the FLAG epitope and amino acids 2–6 of AC 2. The 3' primer, 0J048, spanned base pairs 258–229 of AC2 and included an internal NheI site The 215 bp PCR product was subcloned into pVL1392-AC2 from NotI to NheI to yield the FLAG-AC2 (F-AC2). Recombinants were screened by restriction digests and positives were verified by sequencing the insert through the integration sites. Recombinant plasmids were individually transfected into Sf9 cells along with Baculo-Gold virus DNA at the Protein Expression Core facility. Recombinant baculoviruses were purified by two rounds of limiting dilutions and confirmed as recombinant by dot blots. TPO-AXS (Thyroid Peroxidase) baculovirus (Kendler et al., 1993, Mol. Cell. Endocrinol 93:199–206) was the gift of Dr. R. Magnusson.

7.1.3. EXPRESSION OF AC2 AND F-AC2 IN SF9 CELLS

Sf9 cells were grown in Sf-900 medium (Gibco) or serum-free insect culture medium 1 (Sigma) at 28° C. Cells were infected with recombinant baculoviruses at a multiplicity of infection of about one. Cells were harvested 2–4 days post-infection. When appropriate, PMA or 4a-phorbol-12,13-didecanoate (PDD) were added to the culture medium at 1 $\mu$M and cells were incubated for 20–35 min. When staurosporine was included in the treatment, cells were treated with 1 $\mu$M staurosporine before PMA addition.

Sf9 cells were lysed by nitrogen cavitation or by homogenization in Dounce homogenizers. After treatments, cells were pelleted at 4° C. and washed with lysis buffer containing 20 mM NaHEPES pH 8.0, 4 mM EDTA, 150 mM NaCl, 20 mM Na-phosphate, 20 mM NaF, 10 mM $\beta$-glycerol phosphate 2 mM DTT, and a protease inhibitor cocktail of 2 $\mu$g/ml aprotinin, 4 $\mu$g/ml leupeptin, 1 mM 1,10 phenanthroline, 1 mM phenylmethyl-sulfonyl fluoride. Cells were lysed either by $N_2$ cavitation at 600 p.s.i. for 30 minutes or by homogenization in a glass Dounce homogenizer (25–35 strokes). Supernatant from a low speed spin (1000×g, 10 in) was centrifuged at 100000 ×g for 30'–60' to obtain the membrane fraction. The pellet was resuspended in 10 mM HEPES, pH 8.0, 1 mM EDTA, 200 mM Sucrose, 2 mM DTT and protease inhibitor cocktail to a final concentration of 3–5 mg protein/ml.

7.1.4. ADENYLYL CYCLASE ASSAYS

Assays were performed with 2–5 $\mu$g of membrane protein for 15 min at 32° C. as described in Jacobowitz et al., 1993, J. Biol. Chem. 268:3829–3832; Premont and Iyengar, 1988, J. Biol. Chem. 263:16087–16095. Basal activities were measured in the presence of 5 mM $Mg^{2+}$. Forskolin stimulated activities were measured in the presence of 5 mM $Mg^{2+}$ and 10 $\mu$M forskolin.

7.1.5. IMMUNOAFFINITY PURIFICATION

To solubilize the adenylyl cyclase, 4–5 mg of Sf9 membrane protein per sample were pelleted for 30 min at 60000×g and resuspended in 1 ml of 150 mM NaCl, 5 mM EDTA, 20 mM HEPES pH 8.0, 20% glycerol, 1 mM EGTA and 0.8% dodecyl maltoside (Taussig et al., 1993, J. Biol. Chem. 268:9–12). The suspension was gently shaken at 4° C. for 90 min. Supernatants (60000×g 30 min) were incubated with 15–20 $\mu$l of solubilization buffer preequilibrated Anti-FLAG M2 affinity gel (Kodak) for 3 hours at 4° C. The gel was washed 2–3 times with solubilization buffers containing 0.8%, 0.4% and 0.05% dodecyl maltoside. F-AC2 was eluted by incubation with 0.1 M glycine pH 3.0 for 5–10 min in a volume of 90 $\mu$l. Eluates were immediately neutralized with 10 $\mu$l of 1M NaHEPES pH 8.0 and rapidly frozen on dry ice/acetone.

Electrophoresis and immunoblotting were performed as described in De Vivo, (1992), J. Biol. Chem. 267:18263–18266.

7.1.6. $^{32}$P LABELLING IN SF9 CELLS

Sf9 cells were collected at 48 hours post-infection and washed with phosphate-free Grace's medium supplemented with 20 mM MES pH 6.2. Cells were incubated in the same medium with 0.5 mCi/ml [$^{32}$P]$H_3PO_4$ for 3 hrs and treated with PMA or vehicle, as described. After treatment, the cells (7.5×10$^8$) were washed twice with 40 mls of ice-cold lysis buffer and resuspended in 20 mls of the same buffer. Cells were lysed by homogenization in Dounce homogenizers. Membranes were prepared as described above.

All experiments were repeated thrice with multiple batches of Sf9 cell membranes. Results were qualitatively similar. Typical experiments are shown.

7.2. RESULTS

Figure 6A:
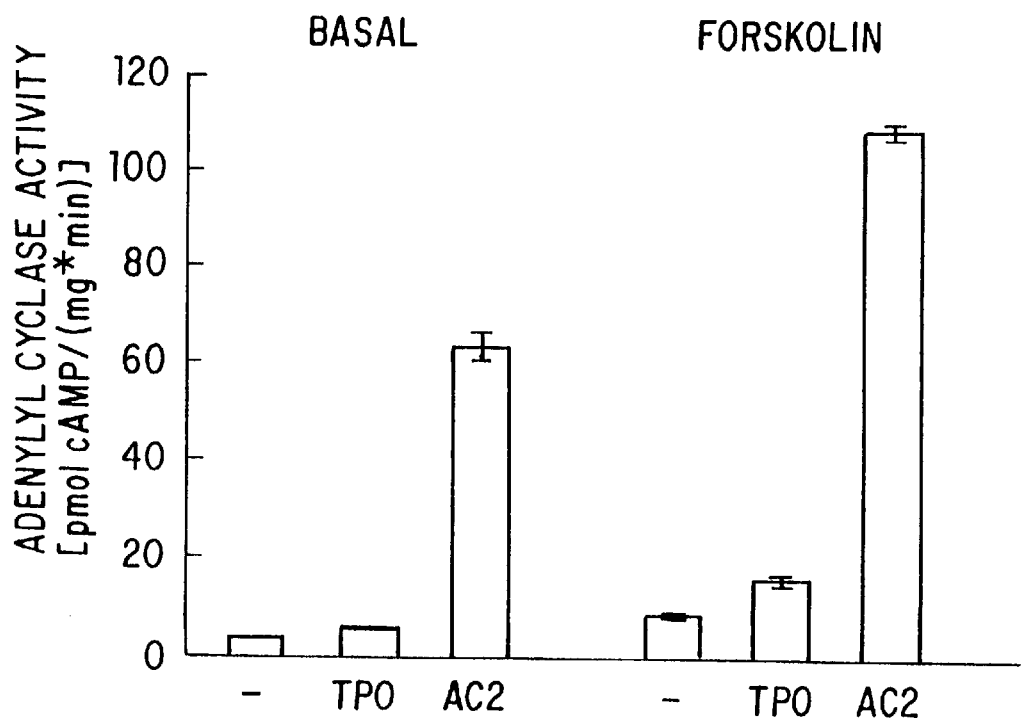
Figure 6B:
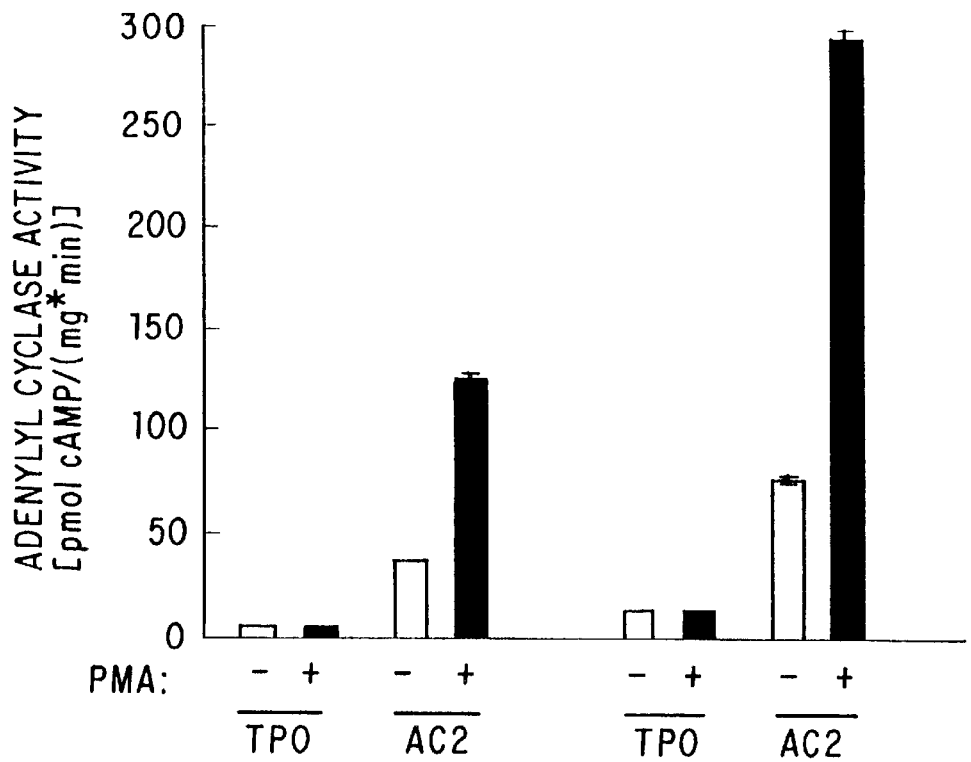
Figure 6C:
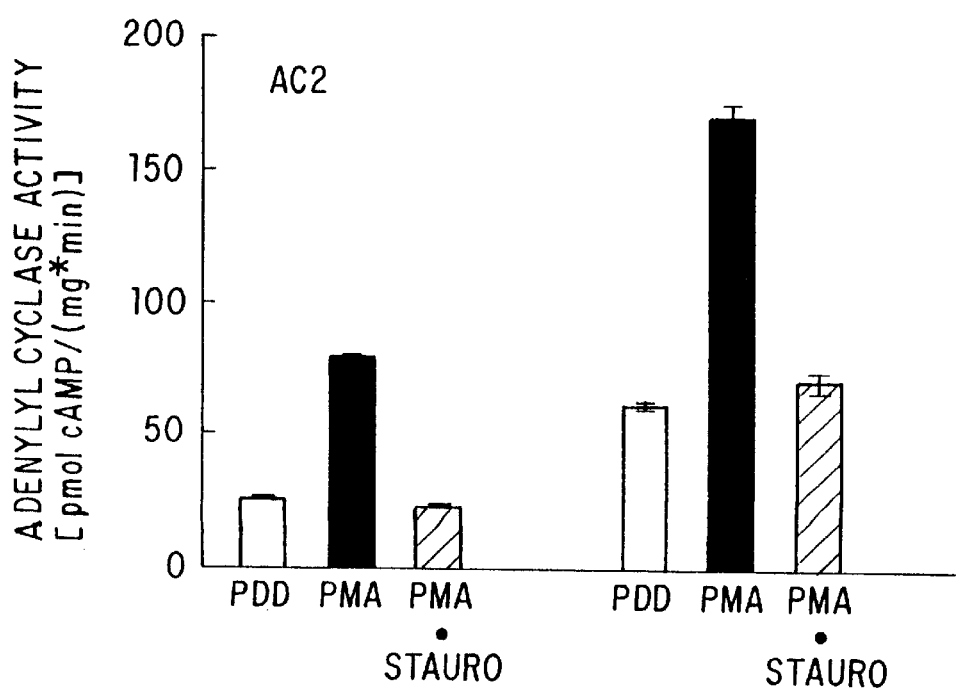

Expression of AC2 in Sf9 cells resulted in a 8–20 fold increase in basal adenylyl cyclase activity in Sf9 cell membranes as compared to uninfected cells or cells infected with baculovirus containing the thyroid peroxidase gene. (FIG. 6A). Treatment of baculovirus-infected cells with PMA for 15 min. prior to lysis resulted in enhancement of the expressed AC 2 activity (FIG. 6B). The inactive phorbol ester, PDD, did not affect activity. Maximal enhancement was observed at 100 nM PMA. We routinely used 1 $\mu$M PMA for treatment. Inclusion of staurosporine during the PMA treatment blocked the increase in activity (FIG. 6C). These data show that AC2 expressed in Sf9 cells can be stimulated by the activation of protein kinase C.

We determined if the activation of protein kinase C was an independent pathway for stimulation of AC 2. Other stimulators such as $G_s\alpha$ and forskolin activate adenylyl cyclase by increasing the $V_{max}$ of the enzyme. We tested if this also occurred with PMA treatment by comparing basal adenylyl cyclase activities at varying concentrations of ATP. Lineweaver-Burke transformation of the data from this experiment show that PMA treatment increases the $V_{max}$ of the enzyme without affecting the $K_m$ for ATP (FIG. 7A), an effect mechanistically similar to that of other stimulators. The greatest extent of sensitization by PMA treatment (about 3- fold) was observed at low $Mg^{2+}$. Increasing the concentration of $Mg^{2+}$ resulted in increases in the basal activity of of the untreated AC 2 with smaller increases for the PMA treated AC 2, resulting in decreased sensitization by PMA at high $Mg^{2+}$ concentrations (FIG. 7B). Stimulation of AC 2 by activated (Q227L) $G_s\alpha$ was enhanced by PMA treatment at all concentrations of $G_s\alpha$ tested but sensitivity to $G_s\alpha$ was unaltered (FIG. 7C). Similarly, PMA treatment resulted in enhancement of the activity observed in the presence of $\alpha_s$ and $\beta\gamma$. These data indicate that PMA treatment results in enhancement of the basal activity by an increase in $V_{max}$ of AC 2 and that the increased activity is observed independently of the action of $G_s\alpha$.

Figure 8B:
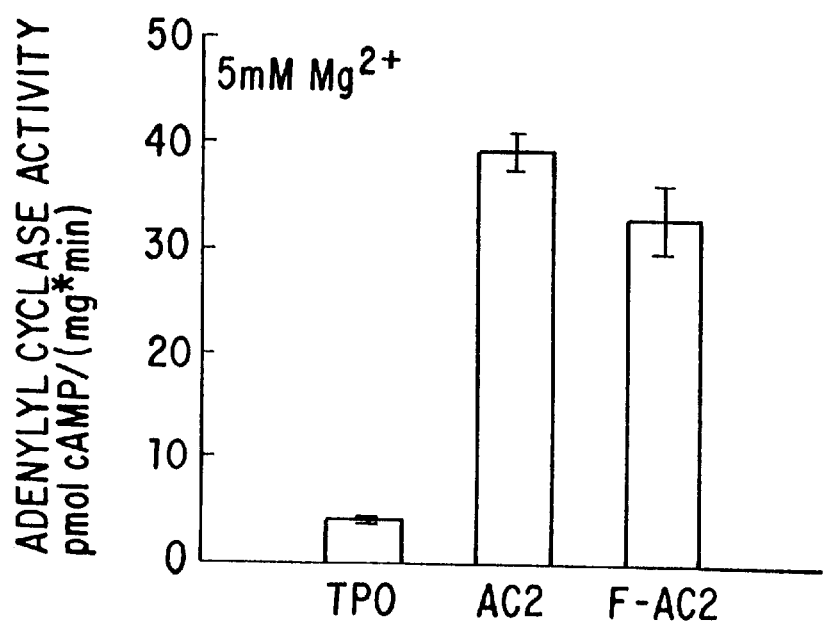
Figure 8A:
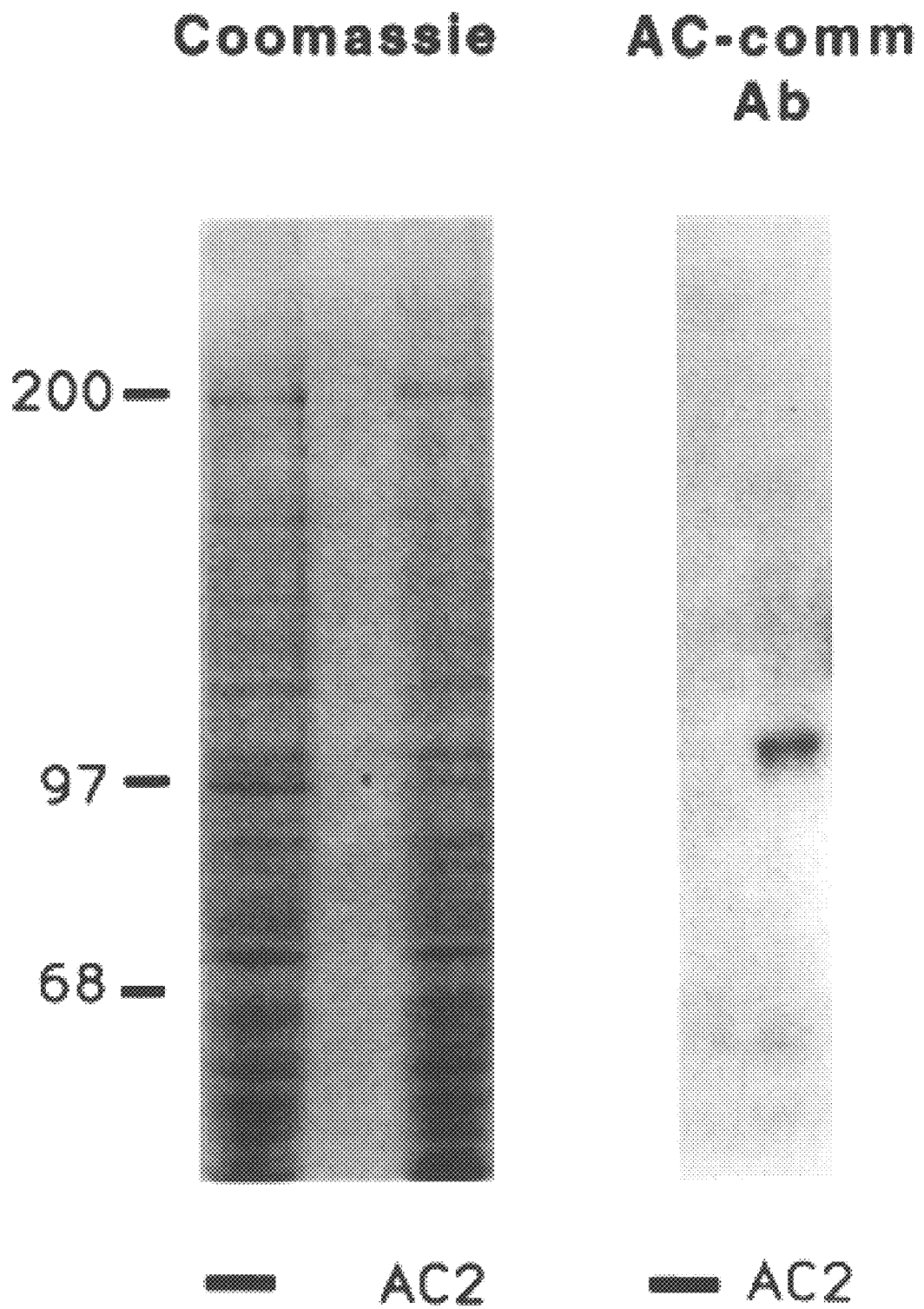

The data in FIGS. 6 and 7 are consistent with phosphorylation of adenylyl cyclase in response to activation of protein kinase C. To determine if this occurred, we attempted to isolate the expressed AC 2. Though adenylyl cyclase activity is substantially increased in AC 2-expressing Sf9 cells, AC 2 is not present at a level where it can be detected by Commassie staining of membrane proteins (FIG. 8A left panel). However, immunoblotting with AC-comm, an anti-peptide antibody to a region common to all mammalian adenylyl cyclases, indicated that an exogenous adenylyl cyclase was being expressed (FIG. 8A, right panel). Thus recombinant baculovirus infection of Sf9 cells probably did not produce sufficient amounts of AC 2 to allow characterization of its phosphorylation state without extensive purification. Conventional methods such as forskolin-affinity chromatography to purify adenylyl cyclase could result in copurification of endogenous adenylyl cyclases of Sf9 cells along with the expressed AC2 and thereby confound interpretation of results of the phosphorylation experiments. Hence we tagged AC 2 at the N-terminus with FLAG, an eight amino acid (DYKDDDDK) (SEQ ID NO:9). The FLAG epitope tagged AC2 (F-AC2) was purified by immunoaffinity chromatography on anti-FLAG antibody agarose, which is commercially available. Expression of F-AC2 resulted in adenylyl cyclase activities similar to that seen with AC2 (FIG. 8B).

Membranes containing F-AC2 were extracted with detergent and the extract was passed over anti-FLAG antibody agarose. The gel was washed and the bound protein was eluted at pH 3.0. When analyzed on SDS- polyacrylamide gels and silver stained, the eluate migrated as a single band of 106 kDa (FIG. 9, left panel). In immunoblot analysis, this protein band was recognized by AC-Comm, the anti-peptide-antiserum against the common region of adenylyl cyclase (FIG. 9, middle panel), and by the anti-FLAG antibody (FIG. 9, right panel). It appears that, F-AC2 can be purified to apparent homogeneity by a single step immunoaffinity chromatography.

Figure 10A:
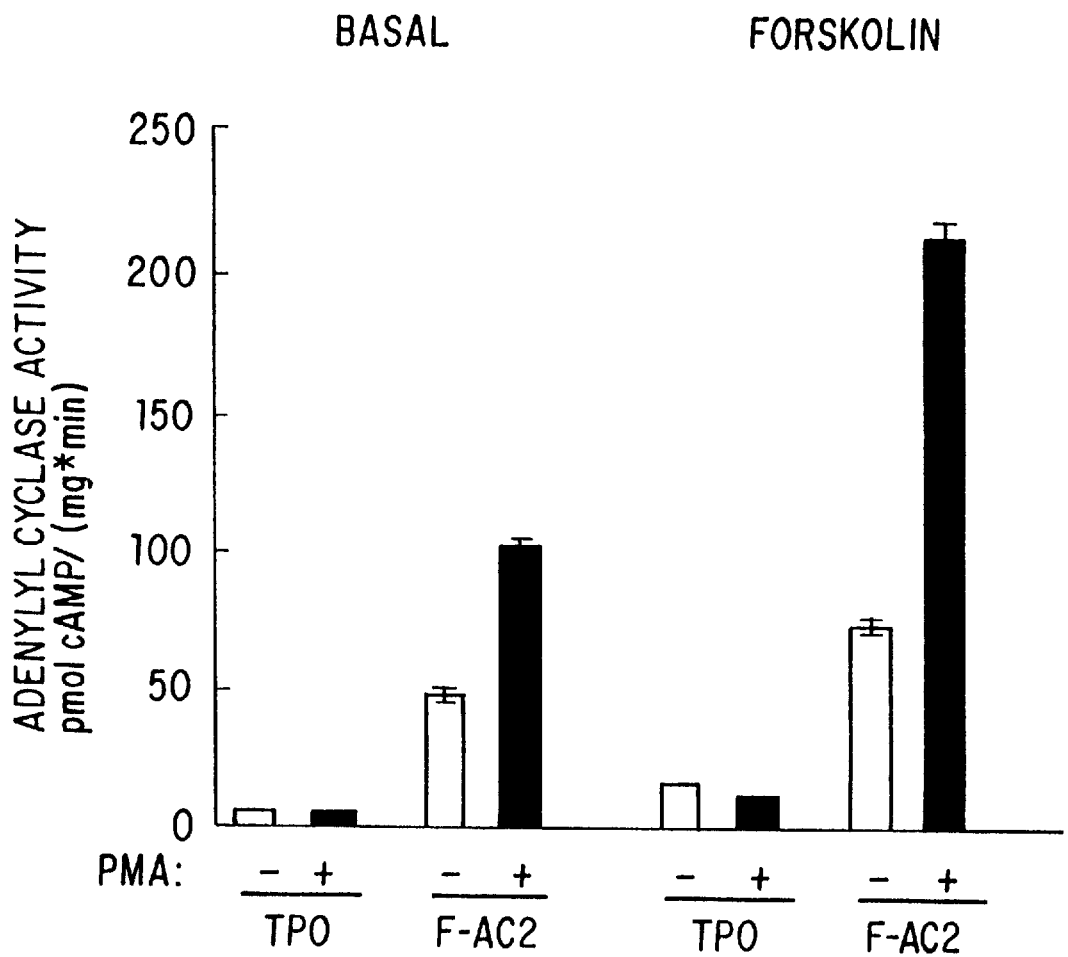
Figure 10B:
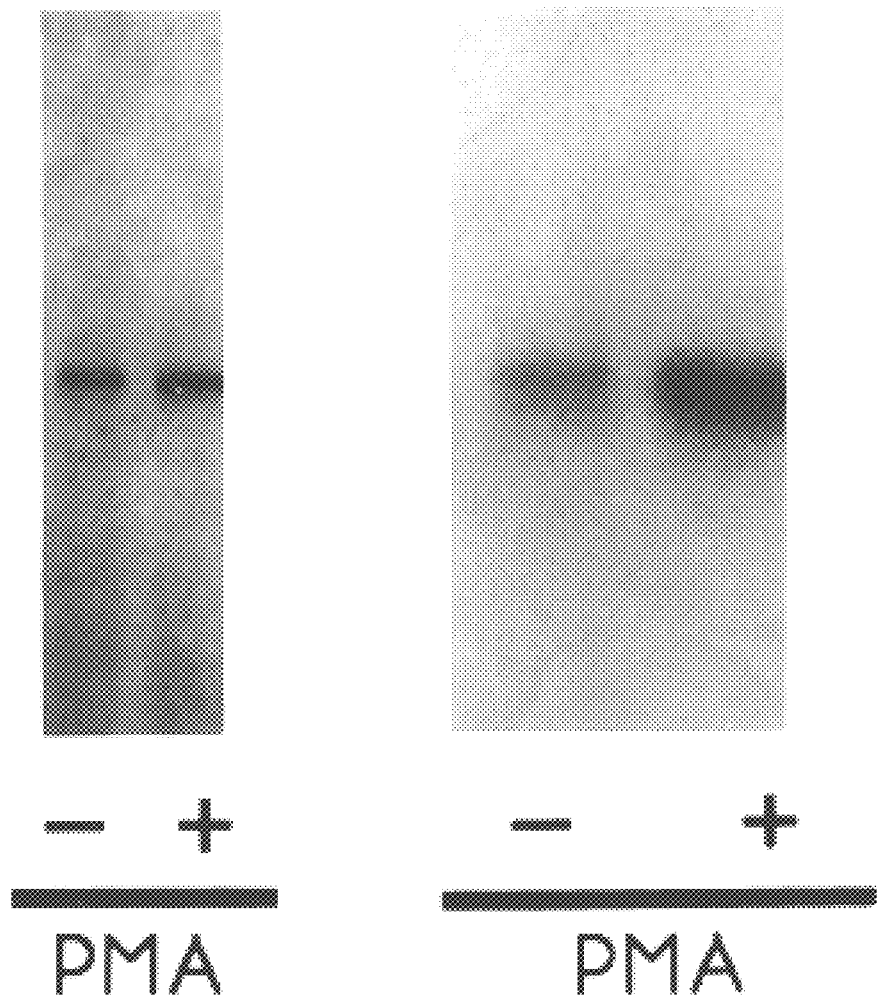

We used immuno-affinity purification to determine if treatment of the F-AC2 baculovirus infected Sf9 cells with PMA resulted in phosphorylation of the F-AC2 and in enhanced adenylyl cyclase activity. For this purpose the cells were labeled with $^{32}$p for 3 hrs before treatment with PMA. In cells expressing F-AC2, PMA treatment resulted in a two-fold increase in basal activity (FIG. 10A). Aliquots of the membranes were extracted and F-AC2 from control and PMA treated cell membranes were individually purified by immunoaffinity chromatography. The eluates from the FLAG-antibody agarose were resolved on SDS-polyacrylamide gels. A single band of 106 kDa was observed (FIG. 10B, left panel). When equivalent amounts of proteins were resolved on SDS-polyacrylamide gels, autoradiographic analysis indicated that treatment of F-AC2 expressing cells with PMA resulted in a three-fold increase in the $^{32}$p incorporated into F-AC2 (FIG. 10B, right panel). The data show that stimulation of protein kinase C results in activation and phosphorylation of AC2.

7.3. DISCUSSION

Upon binding agonists, G protein-coupled receptors interact with and activate heterotrimeric G proteins. The G protein subunits in turn activate effectors, stimulating production of second messengers. In this system, transmembrane signal transduction occurs by sequential protein-protein interactions. In addition to linear signaling, certain effector isoforms are capable of receiving signals from other pathways (Iyengar, 1993, FASEB J. 7:768–775), as exemplified by AC 2. Purified AC 2 can be stimulated by both $\alpha_s$ as well as $\beta\gamma$ subunits (Taussig et al., 1993, J. Biol. Chem. 268:9–12; Tang and Gilman, 1991, Science 254:1500–1503), allowing AC 2 to be positively regulated by both $G_s$ and $G_i$ coupled receptors (Federman et al., 1992, Nature 356:159–161). AC 2 is also activated by stimulation of protein kinase C (Jacobowitz et al., 1993, J. Biol. Chem. 268:3829–3832; Yoshimura and Cooper, 1993, J. Biol. Chem. 268:4604–4607; Lustig et al., 1993, J. Biol. Chem. 268:13900–13905). It was not known if the activation of protein kinase C would result in phosphorylation of AC 2. To establish phosphorylation of AC 2 in an unequivocal fashion, we epitope-tagged AC 2 and then purified the expressed epitope-tagged enzyme with an antibody against the tag. This provided isolation of the heterologously expressed enzyme without any contaminating Sf9 cell adenylyl cyclases. Activation of protein kinase C resulted in enhanced phosphorylation Of adenylyl cyclase and in stimulated activity. This stimulation may be an independent input pathway since it reflects an increase in Vmax of basal activity and is additive with stimulation by $G_s\alpha$.

Many receptors that activate protein kinase C stimulate cAMP production in cells. These include Gq coupled receptors such as angiotensin II (Peytremann et al., 1973, J. Clin. Invest. 52:835–842), muscarinic (Johnson et al., 1991, Mol. Pharmacol. 39:539–546) and $\alpha_1$-adrenergic receptors (Sugden et al., 1985, Nature 314:359–361) as well as receptors that signal through tyrosine kinases such as the NGF (Schubert et al., 1978, Nature 273:718–723) and the B cell antigen receptors (Wiener and Scarpa, 1989, J. Biol. Chem. 264:4324–4328). The added capacity to stimulate cAMP production allows these receptors to produce a multifaceted biological response. For instance, in the pineal gland norepinephrine stimulation of cAMP production through $\alpha_1$-adrenergic receptors in concert with $\beta$-adrenergic receptor stimulation is believed to play a major role in the maintenance of circadian rhythms (Takahashi, 1993, Nature 365:299–300). Additionally, angiotensin II stimulation of steroidogenesis in adrenal cells is mediated by a protein kinase C-dependent increase in intracellular cAMP (Peytremann et al., 1973, J. Clin. Invest. 52:835–842; Bird et al., 1993, Endocrinology 132:932–934).

8. EXAMPLE: SUPPRESSION OF THE TRANSFORMED PHENOTYPE IN THE HUMAN BREAST CANCER CELL LINE MCF-7 BY ELEVATION OF CAMP OR BY THE EXPRESSION OF $G_s\alpha$ MCF-7 cells are a human breast cancer cell line maintained in tissue culture which are widely used as a model system in the laboratory. Proliferation of MCF-7 cells is stimulated by estrogen and thus these cell lines are representative of mammary tissue in vivo (Dickson et al., 1986, Science 232:1540–1543). MCF-7 cells were used to determine if the transfer of the $G_s\alpha^*$ cDNA resulted in expression of the transformed phenotype.

8.1. Materials and Methods

8.1.1 MCF-7 Cell Culture

MCF-7 cells were grown in Dulbecco's modified Eagles Basal Medium (without phenol red) supplemented with 01% fetal bovine serum and antibiotics. Exponentially growing preconfluent cultures were used for all experiments. Cells were transfected with the plasmid pRC-CMV without any insert or with the $G_s\alpha^*$ insert. After transfection, individual clonal lines were isolated and used for further studies.

8.1.2 Transformation Assay

Anchorage independent growth as assessed by colony formation on soft agar plates was used as a criterion for anchorage independent growth. For this, $2.5 \times 10^4$ cells were plated on soft agar plates in medium with 10% serum. Plates were feed weekly. Colonies were scored three weeks later. Detailed procedures used in our laboratory are described in DeVivo et al 1992 J. Biol Chem 267: 18263.

8.1.3 MAP-kinase Assays.

Constitutive MAP-kinase activity of serum starved MCF-7 cells treated with and without 8-Br-cAMP for 24 hr was measured. Cell extracts were chromatographically resolved on Mono-Q columns using fast liquid chromatography and assayed for MAP-kinase activity with a peptide substrate encoding amino acids 662–681 of the epidermal growth factor receptor (Gupta et al 1992 J. Biol Chem 267: 7987).

8.2 Results and Discussion

A MCF-7 clonal line expressing $G_s\alpha^*$ (CMV-$\alpha_s^*$) and a control MCF-7 cell line that had been transfected with the vector without insert (CMV) were tested for their capability to form colonies in soft agar. Under conditions where the control cell line formed more than 500 colonies, the $G_s\alpha^*$ expressing line formed less than 20 colonies. This is shown in FIG. 13a. Three other individual control or $G_s\alpha^*$ expressing clonal lines were further compared for colony formation. Under conditions where the control lines all expressed the transformed phenotype as evidenced by colony formation in soft agar plates all three $G_s\alpha^*$ expressing lines did not show any colony forming ability (FIG. 13b).

The effect of exogenously added 8-Br-cAMP on colony formation by MCF-7 cells in soft agar was also studied. Addition of 10 micromolar 8-Br-cAMP to the soft agar plates resulted in a 50% inhibition of colony formation. At 100 micromolar 8-Br-cAMP there was a complete suppression of colony formation (FIG. 14).

Activation of MAP-kinase is essential for the transformation (Crowley et al 1994 Cell 77: 841). Hence it appeared likely that transformed cells would have constitutive MAP-kinase activity and that elevation of cAMP would be able to inhibit this activity. The effect of 8-Br-cAMP on the constitutive MAP-kinase activity of serum starved MCF-7 cells was measured. Non-transformed cells such as NIH-3T3 or RAT-1 upon serum starvation achieve quiescence and do not have any measurable MAP-kinase activity. In contrast, MCF-7 cells which are transformed showed significant levels of MAP-kinase activity. This constitutive MAP-kinase activity was suppressed when the cells were incubated with 8-Br-cAMP (FIG. 15).

These observations in the MCF-7 cells lines show that the observations on the murine NIH-3T3 fibroblasts are also applicable to human cells and that expression of $G_s\alpha^*$ and elevation of cAMP levels results in suppression of the transformed state.

Various publications are cited herein which are hereby incorporated, by reference, in their entireties.

---

What is claimed is:

1. A method of reducing or reversing the malignant phenotype of malignant mammary cells in a human subject comprising introducing a gene encoding a mutant activated $G_s\alpha$ protein having SEQ ID NO: 1, except that the glutamine residue at position 227 is replaced by a leucine residue, into malignant mammary cells of the subject wherein a therapeutically effective amount of a mutant activated $G_s\alpha$ protein is produced in the cells.

2. The method according to claim 1, in which the mutant activated $G_s\alpha$ gene is introduced into the malignant mammary cells by a method comprising transfecting the malignant mammary cells with a viral vector comprising a nucleic acid encoding the mutant activated $G_s\alpha$ protein.

3. The method according to claim 2 in which the viral vector is an adenovirus vector.

4. A method of reducing proliferation of vascular smooth muscle cells in a subject comprising introducing a gene encoding a mutant activated $G_s\alpha$ protein having SEO. ID NO:1. except that the glutamine residue at position 227 is replaced by a leucine residue, into the vascular smooth muscle cells such that a therapeutically effective amount of the mutant activated $G_s\alpha$ protein is produced in the cells.

5. The method according to claim 4, in which the mutant activated $G_s\alpha$ gene is introduced into the vascular smooth muscle cells by a method comprising transfecting the vascular smooth muscle cells with a viral vector comprising a nucleic acid encoding the mutant activated $G_s\alpha$ protein.

6. The method according to claim 5, in which the viral vector is an adenovirus vector.

7. A method of producing bronchodilation comprising introducing into bronchial smooth muscle cells, a gene encoding a mutant activated $G_s\alpha$ protein having SEQ ID NO:1. except that the glutamine residue at position 227 is replaced by a leucine residue, such that a therapeutically effective amount of the mutant activated $G_s\alpha$ protein is produced in the cells.

8. The method according to claim 7, in which the mutant activated $G_s\alpha$ gene is introduced into the bronchial smooth muscle cells by a method comprising transfecting the bronchial smooth muscle cells with a viral vector comprising a nucleic acid encoding the mutant activated $G_s\alpha$ protein.

9. The method according to claim 8, in which the viral vector is an adenovirus vector.

* * * * *

UNITED STATES PATENT AND TRADEMARK OFFICE
CERTIFICATE OF CORRECTION

| | | |
|---|---|---|
| PATENT NO. | : 6,034,071 | |
| APPLICATION NO. | : 08/307896 | |
| DATED | : March 7, 2000 | |
| INVENTOR(S) | : Srinivas Ravi V. Iyengar | |

It is certified that error appears in the above-identified patent and that said Letters Patent is hereby corrected as shown below:

Col. 1 lines 5-8 should read:

-- This invention was made with government support under ~~grand~~ grant number CA-44998 awarded by the National Institutes of Health. The government has certain rights in the invention. --

Signed and Sealed this

Twenty-second Day of September, 2009

David J. Kappos
*Director of the United States Patent and Trademark Office*